United States Patent
Brown et al.

(10) Patent No.: US 11,661,604 B2
(45) Date of Patent: *May 30, 2023

(54) METHODS AND COMPOSITIONS FOR INHIBITING EXPRESSION OF LDHA

(71) Applicant: Dicerna Pharmaceuticals, Inc., Lexington, MA (US)

(72) Inventors: Bob D. Brown, Lexington, MA (US); Henryk T. Dudek, Lexington, MA (US); Utsav Saxena, Lexington, MA (US); Natalie Pursell, Lexington, MA (US); Cheng Lai, Lexington, MA (US); Weimin Wang, Lexington, MA (US); Rachel Storr, Lexington, MA (US); Naim Nazef, Lexington, MA (US); Boyoung Kim, Lexington, MA (US)

(73) Assignee: DICERNA PHARMACEUTICALS, INC., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/022,696

(22) Filed: Sep. 16, 2020

(65) Prior Publication Data

US 2021/0062199 A1 Mar. 4, 2021

Related U.S. Application Data

(63) Continuation of application No. 16/755,342, filed as application No. PCT/US2018/055735 on Oct. 12, 2018, now Pat. No. 11,286,488.

(Continued)

(51) Int. Cl.
*C12N 15/113* (2010.01)
*A61K 9/00* (2006.01)

(52) U.S. Cl.
CPC ........ *C12N 15/1137* (2013.01); *A61K 9/0019* (2013.01); *C12N 2310/11* (2013.01); *C12N 2310/315* (2013.01); *C12N 2310/321* (2013.01); *C12N 2310/322* (2013.01); *C12N 2310/344* (2013.01); *C12N 2310/351* (2013.01)

(58) Field of Classification Search
CPC ............ A61K 31/7088; C12N 15/1137; C12N 2310/11; C12N 2310/14
See application file for complete search history.

(56) References Cited

U.S. PATENT DOCUMENTS 9,487,809 B2  11/2016 Zhou et al.
10,011,856 B2  7/2018 Zhou et al.
(Continued)

FOREIGN PATENT DOCUMENTS

WO   WO-2004071405 A2   8/2004
WO   WO-2005089287 A2   9/2005
(Continued)

OTHER PUBLICATIONS

International Search Report and Written Opinion issued by the United States Patent Office as International Searching Authority for International Application No. PCT/US2018/055735, dated Feb. 4, 2019.

(Continued)

*Primary Examiner* — Terra C Gibbs
(74) *Attorney, Agent, or Firm* — Andrea L. C. Reid; Gang Wang; Dechert LLP

(57) ABSTRACT

This disclosure relates to oligonucleotides, compositions and methods useful for reducing LDHA expression, particularly in hepatocytes.

20 Claims, 12 Drawing Sheets

Specification includes a Sequence Listing.

Related U.S. Application Data

(60) Provisional application No. 62/726,950, filed on Sep. 4, 2018, provisional application No. 62/572,398, filed on Oct. 13, 2017, provisional application No. 62/572,403, filed on Oct. 13, 2017.

(56) References Cited

U.S. PATENT DOCUMENTS

| | | |
|---|---|---|
| 10,351,854 B2 | 7/2019 | Brown et al. |
| 10,738,311 B2 | 8/2020 | Brown et al. |
| 11,053,502 B1 | 7/2021 | Brown et al. |
| 2008/0113351 A1 | 5/2008 | Naito et al. |
| 2010/0173973 A1 | 7/2010 | Brown |
| 2011/0207799 A1 | 8/2011 | Rozema et al. |
| 2011/0288147 A1 | 11/2011 | Brown |
| 2012/0003156 A1 | 1/2012 | Dang et al. |
| 2012/0121515 A1 | 5/2012 | Dang et al. |
| 2019/0106699 A1 | 4/2019 | Khvorova et al. |
| 2019/0323014 A1 | 10/2019 | Brown et al. |
| 2020/0283775 A1 | 9/2020 | Brown et al. |
| 2021/0180068 A1 | 6/2021 | Brown et al. |

FOREIGN PATENT DOCUMENTS

| | | |
|---|---|---|
| WO | WO-2006006948 A2 | 1/2006 |
| WO | WO-2008136902 A1 | 11/2008 |
| WO | WO-2010033225 A2 | 3/2010 |
| WO | WO-2011104169 A1 | 9/2011 |
| WO | WO-2011150241 A2 | 12/2011 |
| WO | WO-2012156513 A1 | 11/2012 |
| WO | WO-2013074974 A2 | 5/2013 |
| WO | WO-2013166121 A1 | 11/2013 |
| WO | 2016057932 A1 | 4/2016 |
| WO | 2016100401 A1 | 6/2016 |
| WO | 2016100635 A1 | 6/2016 |
| WO | 2019075419 A1 | 4/2019 |

OTHER PUBLICATIONS

Adeva et al., "Enzymes involved in I-lactate metabolism in humans," Mitochondrion. 2013; 13(6): 615-629.

Aijima et al., "A case of suspected primary hyperoxaluria with severe teeth mobility," Japanese Journal of Oral and Maxillofacial Surgery. 2010; 56: 710-714, Only Abstract considered.

Allerson et al., "Fully 2'-modified oligonucleotide duplexes with improved in vitro potency and stability compared to unmodified small interfering RNA," J Med Chem. 2005; 48(4):901-4.

Dutta et al., "Inhibition of glycolate oxidase with Dicer-substrate siRNA reduces calcium oxalate deposition in a mouse model of primary hyperoxaluria type 1," Mol. Ther. 2016; 24:770-778.

International Search Report and Written Opinion issued by the European Patent Office as International Searching Authority for International Application No. PCT/US2015/054959, dated Mar. 29, 2016 (17 pages).

Langhammer et al., "LDH-A gene suppression affects cell growth of colon carcinoma xenografts but not in culture conditions," European Journal of Cancer Supplements. 2008; 6(9): 21-22.

Liebow et al., "An investigational RNAi therapeutic targeting glycolate oxidase reduces oxalate production in models of primary hyperoxaluria," J. Am. Soc. Nephrol. 2017; 28:494-503.

Miao et al., "Lactate dehydrogenase a in cancer: A promising target for diagnosis and therapy: LDHA in Cancer," International Union of Biochemistry and Molecular Biology Life. 2013; 65(11): 904-910.

Sebestyén et al., "Targeted in vivo delivery of siRNA and an endosome-releasing agent to hepatocytes," RNA Interference. Humana Press, New York, NY, 2015. 163-186.

Sheng et al., "Knockdown of lactate dehydrogenase a suppresses tumor growth and metastasis of human hepatocellular carcinoma," FEBS Journal. 2012; 279(20): 3898-3910.

Wang et al., "LDH-A silencing suppresses breast cancer tumorigenicity through induction of oxidative stress mediated mitochondrial pathway apoptosis," Breast Cancer Research and Treatment. 2012; 131(3): 791-800.

Zeng, "Why We Think Arrowhead Research is Undervalued," Seeking Alpha [online], Jul. 25, 2013, [retrieved on Jun. 28, 2019], internet: <URL:https://seekingalpha.com/article/1519452-why-we-thinkarrowhead-research-is-undervalued>.

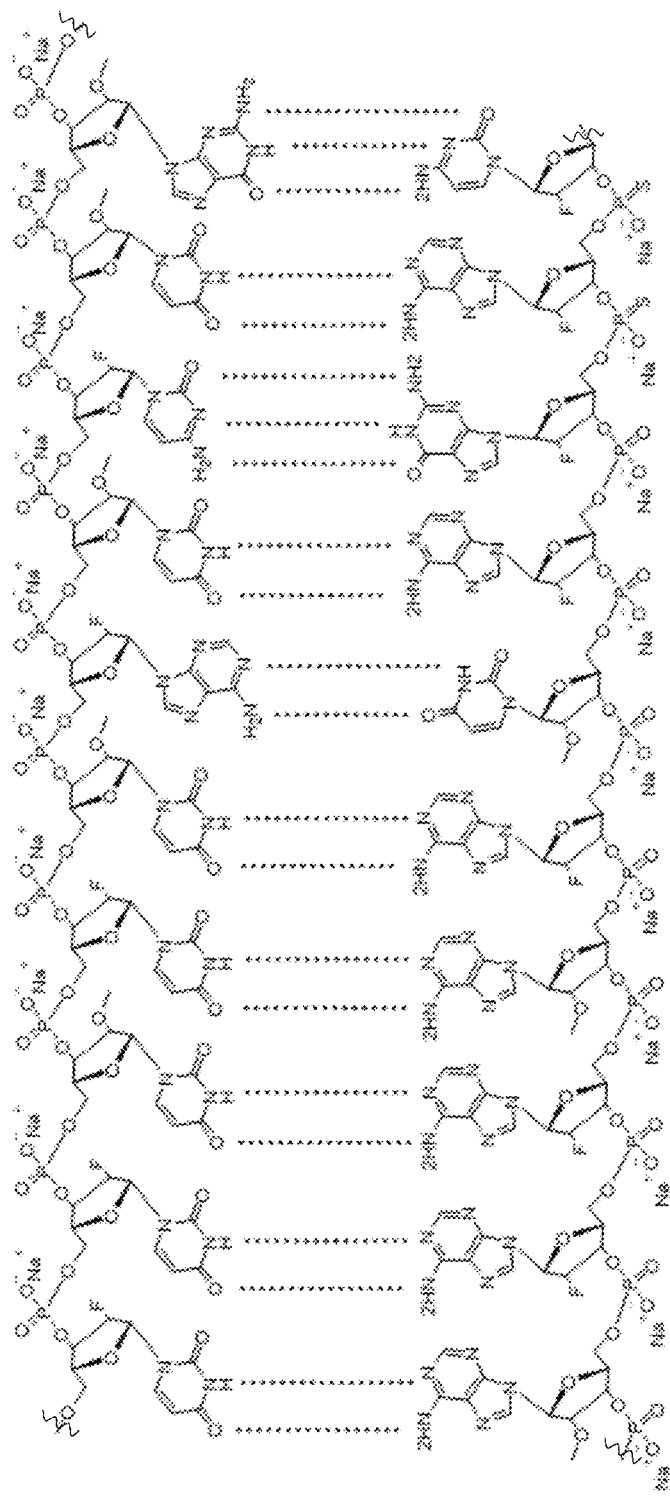
FIG. 3 – cont.

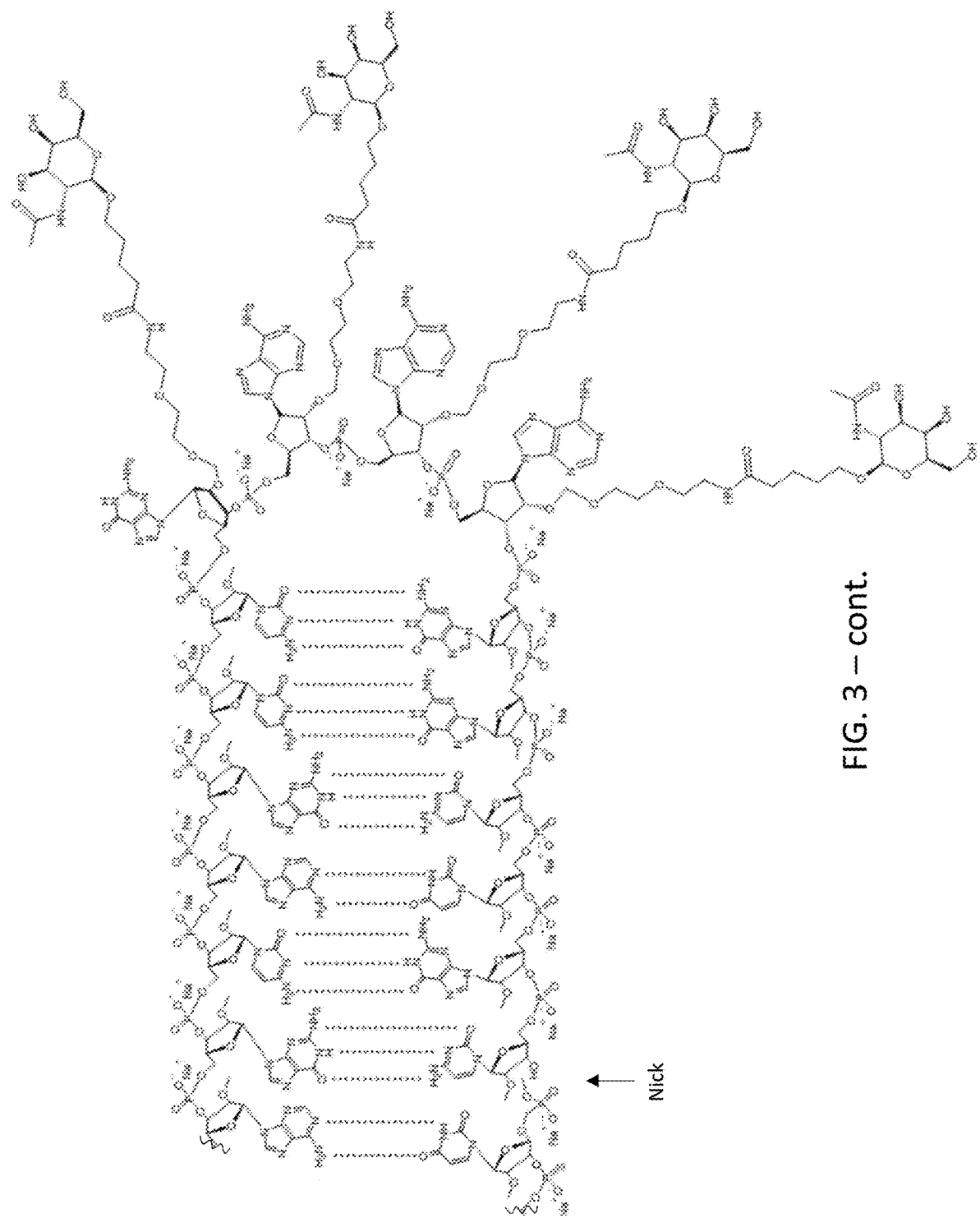
FIG. 3 — cont.

**** = p < 0.0001 compared with control
*** = p ≤ 0.001 compared with control
** = p ≤ 0.01 compared with control \*\*\*\*  = $P < 0.0001$ compared with control
\*\*   = $P \leq 0.01$ compared with control
\*    = $P \leq 0.05$ compared with control

SEQUENCE LISTING

<160> NUMBER OF SEQ ID NOS: 2

<210> SEQ ID NO 1
<211> LENGTH: 22
<212> TYPE: DNA

```
<213> ORGANISM: Artificial Sequence
<220> FEATURE:
<223> OTHER INFORMATION: Synthetic polynucleotide

<400> SEQUENCE: 1
ucagauaaaa aggacaacau gg                                              22

<210> SEQ ID NO 2
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 2
auguuguccu uuuuaucuga gcagccgaaa ggcugc                               36
```

METHODS AND COMPOSITIONS FOR INHIBITING EXPRESSION OF LDHA

RELATED APPLICATION

This application is a continuation application of U.S. patent application Ser. No. 16/755,342, filed Apr. 10, 2020, which claims the benefit under 35 U.S.C. § 119(e) to U.S. Provisional Application No. 62/726,950, filed Sep. 4, 2018, entitled "METHODS AND COMPOSITIONS FOR INHIBITING EXPRESSION OF LDHA," U.S. Provisional application No. 62/572,403, filed Oct. 13, 2017, entitled "METHODS AND COMPOSITIONS FOR INHIBITING EXPRESSION OF LDHA," and U.S. Provisional application No. 62/572,398, filed Oct. 13, 2017, entitled "METHODS AND COMPOSITIONS FOR INHIBITING EXPRESSION OF LDHA," the entire contents of which are incorporated herein by reference.

REFERENCE TO SEQUENCE LISTING

The instant application contains a Sequence Listing which has been submitted electronically in ASCII format and is hereby incorporated by reference in its entirety. Said ASCII copy, created on Sep. 7, 2021, is named 170311_SL.txt and is 806 bytes in size.

FIELD OF THE INVENTION

The present invention relates to oligonucleotides, compositions, and methods for reducing gene expression and/or activity.

BACKGROUND OF THE INVENTION

Primary Hyperoxalurias (PHs) are autosomal recessive disorders caused by the overproduction of oxalate leading to calcium oxalate precipitation in the kidney and eventually end stage renal disease. There are three forms of PH designated as PH types 1 (PH1), 2 (PH2) and 3 (PH3) as well as idiopathic hyperoxaluria. Lactate dehydrogenase (LDH) has been identified as a target for reducing hepatic oxalate production as it is the key enzyme responsible for converting glyoxylate to oxalate, the last step of oxalate metabolism in the liver. RNAi oligonucleotides targeting genes encoding LDH subunits have been developed.

BRIEF SUMMARY OF THE INVENTION

The present invention is based, at least in part, upon the identification of potent oligonucleotides producing durable RNAi-based knockdown of LDH protein, thereby reducing LDH enzyme activity. In some embodiments, RNAi oligonucleotides disclosed herein have, among other characteristics, improved stability, improved bioavailability, improved hepatic targeting, and/or improved durational effects on gene knockdown compared with prior oligonucleotides. In some embodiments, RNAi oligonucleotides disclosed herein comprise nicked tetraloop structures to which are conjugated N-Acetylgalactosamine (GalNAc) moieties for specifically delivering the oligonucleotides to hepatocytes, thereby avoiding or minimizing potential undesired effects in other tissues, such as muscle, skin, or uterus. In some embodiments, RNAi oligonucleotides disclosed herein are useful for reducing hepatic oxalate production in a subject, e.g., a patient having a primary hyperoxaluria. In some embodiments, RNAi oligonucleotides disclosed herein are useful for reducing urine oxalate levels. In some embodiments, RNAi oligonucleotides disclosed herein are useful for treating primary hyperoxaluria, including PH1, PH2 and/or PH3, as well as idiopathic hyperoxaluria.

Some aspects of the present disclosure provide an oligonucleotide for reducing expression of LDHA, the oligonucleotide comprising an antisense strand having a sequence set forth as UCAGAUAAAAAGGACAACAUGG (SEQ ID NO: 1) and a sense strand having a sequence set forth as (SEQ ID NO: 2)
AUGUUGUCCUUUUUAUCUGAGCAGCCGAAAGGCUGC.

In some embodiments, the oligonucleotide comprises at least one modified nucleotide. In some embodiments, all of the nucleotides of the oligonucleotide are modified. In some embodiments, the modified nucleotide comprises a 2'-modification. In some embodiments, the 2'-modification is a 2'-fluoro or 2'-O-methyl. In some embodiments, one or more of the following positions are modified with a 2'-O-methyl: positions 1, 2, 4, 6, 7, 12, 14, 16, 18-26, or 31-36 of the sense strand and/or positions 1, 6, 8, 11-13, 15, 17, or 19-22 of the antisense strand. In some embodiments, all of positions 1, 2, 4, 6, 7, 12, 14, 16, 18-26, and 31-36 of the sense strand and positions 1, 6, 8, 11-13, 15, 17, and 19-22 of the antisense strand are modified with a 2'-O-methyl. In some embodiments, one or more of the following positions are modified with a 2'-fluoro: positions 3, 5, 8-11, 13, 15, or 17 of the sense strand and/or positions 2-5, 7, 9, 10, 14, 16, or 18 of the antisense strand. In some embodiments, all of positions 3, 5, 8-11, 13, 15, or 17 of the sense strand and positions 2-5, 7, 9, 10, 14, 16, and 18 of the antisense strand are modified with a 2'-fluoro.

In some embodiments, the oligonucleotide comprises at least one modified internucleotide linkage. In some embodiments, the at least one modified internucleotide linkage is a phosphorothioate linkage. In some embodiments, the oligonucleotide has a phosphorothioate linkage between one or more of: positions 1 and 2 of the sense strand, positions 1 and 2 of the antisense strand, positions 2 and 3 of the antisense strand, positions 3 and 4 of the antisense strand, positions 20 and 21 of the antisense strand, and positions 21 and 22 of the antisense strand. In some embodiments, the oligonucleotide has a phosphorothioate linkage between each of: positions 1 and 2 of the sense strand, positions 1 and 2 of the antisense strand, positions 2 and 3 of the antisense strand, positions 3 and 4 of the antisense strand, positions 20 and 21 of the antisense strand, and positions 21 and 22 of the antisense strand.

In some embodiments, the uridine at the first position of the antisense strand comprises a phosphate analog.

In some embodiments, the oligonucleotide comprises the following structure at position 1 of the antisense strand:

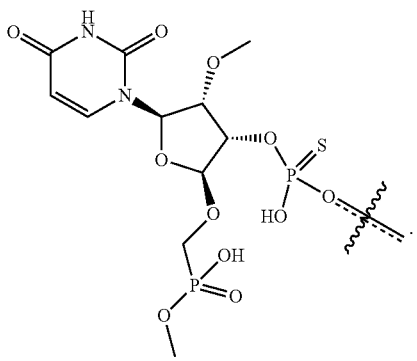

In some embodiments, one or more of the nucleotides of the -GAAA-sequence on the sense strand is conjugated to a monovalent GalNac moiety. In some embodiments, each of the nucleotides of the -GAAA- sequence on the sense strand is conjugated to a monovalent GalNac moiety. In some embodiments, the -GAAA- motif comprises the structure:

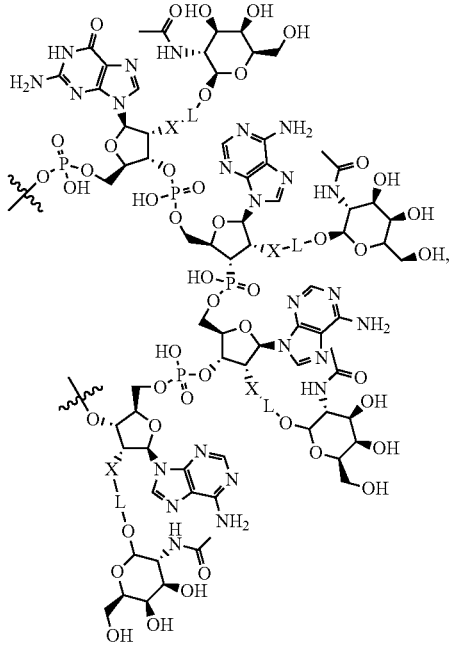

wherein:

L represents a bond, click chemistry handle, or a linker of 1 to 20, inclusive, consecutive, covalently bonded atoms in length, selected from the group consisting of substituted and unsubstituted alkylene, substituted and unsubstituted alkenylene, substituted and unsubstituted alkynylene, substituted and unsubstituted heteroalkylene, substituted and unsubstituted heteroalkenylene, substituted and unsubstituted heteroalkynylene, and combinations thereof; and X is a O, S, or N.

In some embodiments, L is an acetal linker. In some embodiments, X is O.

In some embodiments, the -GAAA- sequence comprises the structure:

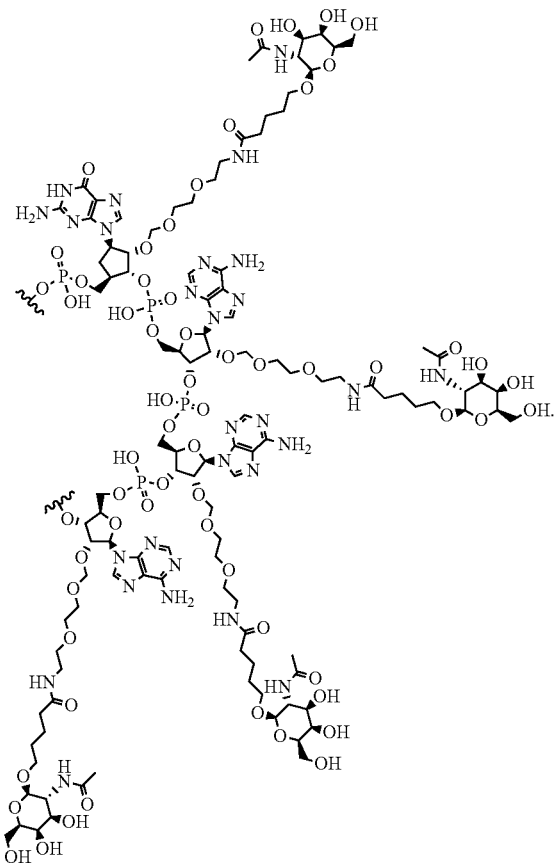 [SMILES: *O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@@H]1[C@@H](COP(=O)(O)O*)C[C@@H](n2cnc3c(=O)[nH]c(N)nc32)[C@@H]1OCOCCOCCNC(=O)CCCCO[C@@H]1O[C@H](CO)[C@H](O)[C@H](O)[C@H]1NC(C)=O]

In some embodiments, the oligonucleotide for reducing expression of LDHA comprises an antisense strand having a sequence set forth as UCAGAUAAAAAGGACAA-CAUGG (SEQ ID NO: 1) and a sense strand having a sequence set forth as AUGUUGUCC-UUUUUAUCUGAGCAGCCGAAAGGCUGC (SEQ ID NO: 2), wherein all of positions 1, 2, 4, 6, 7, 12, 14, 16, 18-26, and 31-36 of the sense strand and positions 1, 6, 8, 11-13, 15, 17, and 19-22 of the antisense strand are modified with a 2'-O-methyl, and all of positions 3, 5, 8-11, 13, 15, or 17 of the sense strand and positions 2-5, 7, 9, 10, 14, 16, and 18 of the antisense strand are modified with a 2'-fluoro;

wherein the oligonucleotide has a phosphorothioate linkage between each of: positions 1 and 2 of the sense strand, positions 1 and 2 of the antisense strand, positions 2 and 3 of the antisense strand, positions 3 and 4 of the antisense strand, positions 20 and 21 of the antisense strand, and positions 21 and 22 of the antisense strand;

wherein the oligonucleotide comprises the following structure at position 1 of the antisense strand:

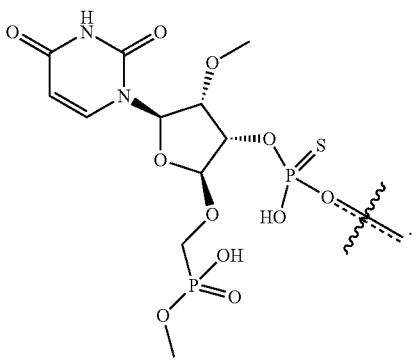

wherein each of the nucleotides of the -GAAA- sequence on the sense strand is conjugated to a monovalent GalNac moiety comprising the structure:

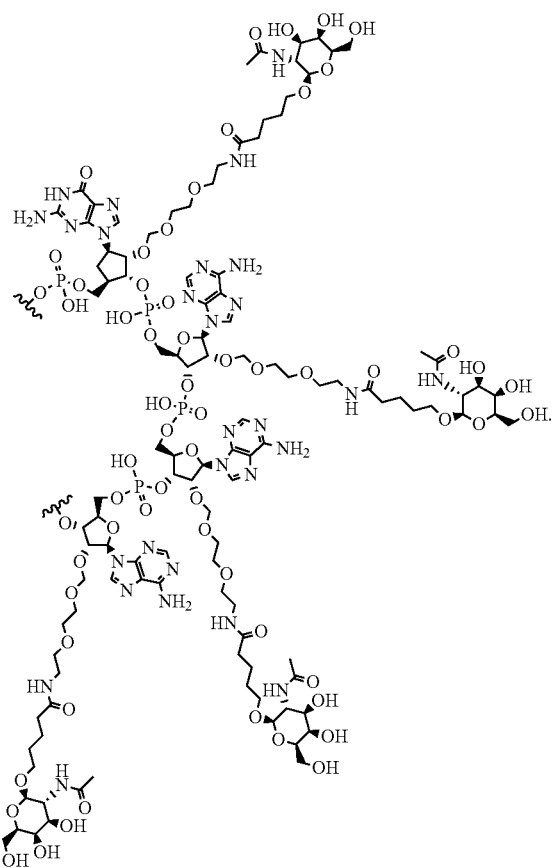 [SMILES: *O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@@H]1[C@@H](COP(=O)(O)O*)C[C@@H](n2cnc3c(=O)[nH]c(N)nc32)[C@@H]1OCOCCOCCNC(=O)CCCCO[C@@H]1O[C@H](CO)[C@H](O)[C@H](O)[C@H]1NC(C)=O]

Other aspects of the present disclosure provide a composition comprising any of the oligonucleotide described herein and Na$^+$ counterions.

A composition having the chemical structure as depicted in FIG. 3 is also provided.

Other aspects of the present disclosure provide methods of delivering an oligonucleotide to a subject, the method comprising administering any of the composition or oligonucleotide described herein to the subject. In some embodiments, the subject has or is at risk of having PH1, PH2, PH3, and/or idiopathic hyperoxaluria, the method comprising reducing expression of LDHA protein in hepatocytes in the subject by administering the oligonucleotide described herein to the subject.

Other aspects of the present disclosure provide the use of an oligonucleotide or composition described herein for the treatment of a subject having or at risk of having a primary hyperoxaluria, the treatment comprising administering the oligonucleotide or composition to the subject. In some embodiments, the oligonucleotide or composition is administered to the subject intravenously or subcutaneously.

BRIEF DESCRIPTION OF THE DRAWINGS

The accompanying drawings, which are incorporated in and constitute a part of this specification, illustrate certain embodiments, and together with the written description, serve to provide non-limiting examples of certain aspects of the compositions and methods disclosed herein.

FIG. 8A shows the changes in the absolute value of urinary oxalate (UOX) content in these patients over the course of study. For the 1.5 mg/kg dose group, n=2 after D57. For the 3 mg/kg dose group n=2 after D57. For the 6 mg/kg dose group, n=2 and n=1 after D15. FIG. 8B shows 24 hr urinary oxalate (UOX) % change from baseline in patients in the 1.5 mg/kg dose group and 3 mg/kg dose group over the course of study.

DETAILED DESCRIPTION OF THE INVENTION

Figure 1A:
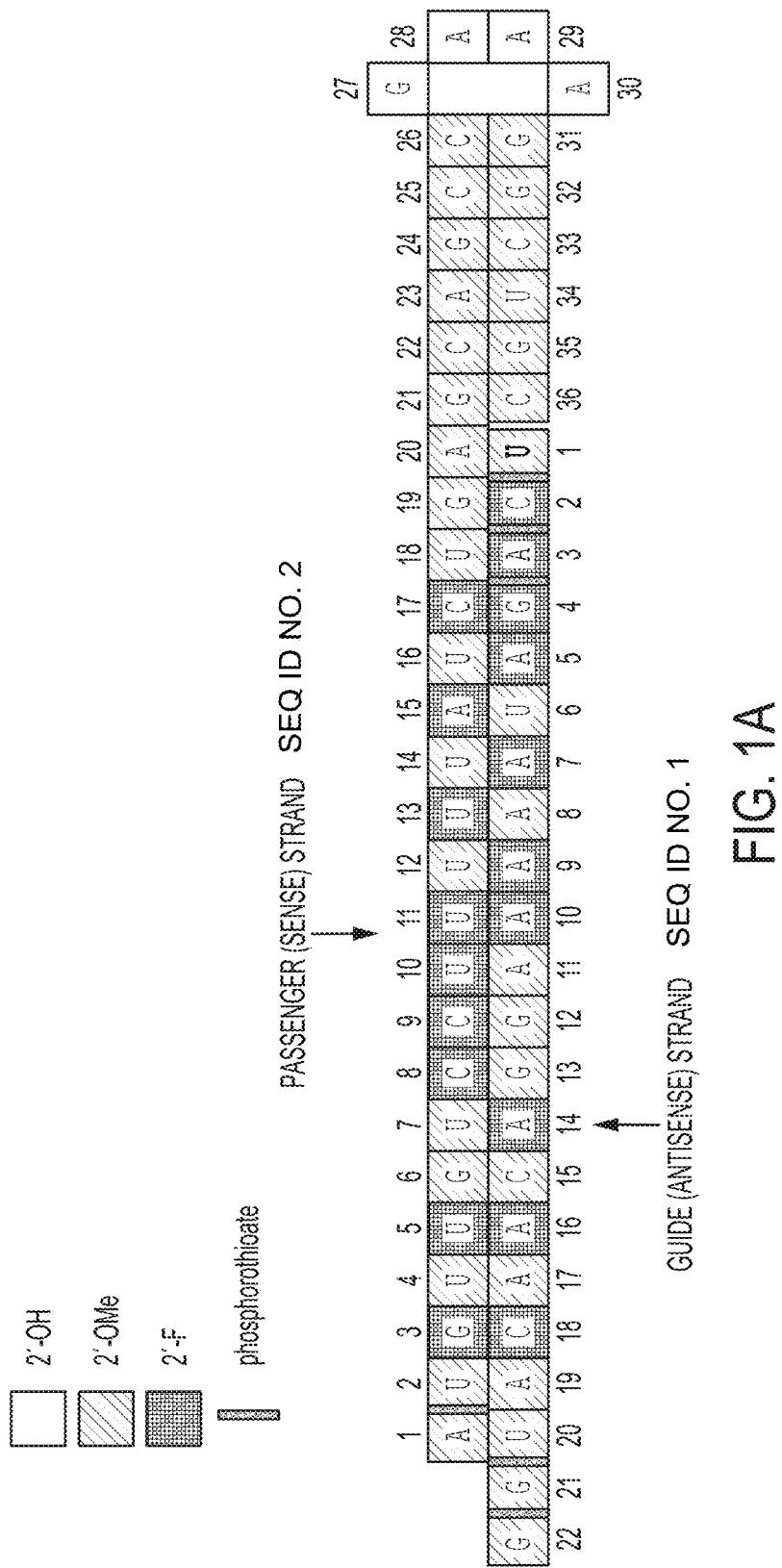
FIG. 1A is a schematic showing a non-limiting example of an RNAi oligonucleotide having a guide (antisense) strand with a region of complementarity with LDHA mRNA.

According to some aspects, the disclosure provides RNAi oligonucleotides targeting LDHA mRNA that are effective for reducing LDH enzyme activity. In some embodiments, these RNAi oligonucleotides are useful for the reduction of LDHA in, for example, liver cells (e.g., hepatocytes). In some embodiments, repression of hepatic LDH activity using RNAi oligonucleotides disclosed herein provides a therapeutic approach to treat primary hyperoxalurias including PH1, PH2 and/or PH3, as well as idiopathic hyperoxaluria.

Further aspects of the disclosure, including a description of defined terms, are provided below.

I. Definitions

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9% 8% 7%, 6%, 5%, 4%, 3%, 2%, 1%, or less in either direction (greater than or less than) of the stated reference value unless otherwise stated or otherwise evident from the context (except where such number would exceed 100% of a possible value).

Administering: As used herein, the terms "administering" or "administration" means to provide a substance (e.g., an oligonucleotide) to a subject in a manner that is pharmacologically useful (e.g., to treat a condition in the subject).

Asialoglycoprotein receptor (ASGPR): As used herein, the term "Asialoglycoprotein receptor" or "ASGPR" refers to a bipartite C-type lectin formed by a major 48 kDa (ASGPR-1) and minor 40 kDa subunit (ASGPR-2). ASGPR is primarily expressed on the sinusoidal surface of hepatocyte cells and has a major role in binding, internalization, and subsequent clearance of circulating glycoproteins that contain terminal galactose or N-acetylgalactosamine residues (asialoglycoproteins).

Attenuates: As used herein, the term "attenuates" means reduces or effectively halts. As a non-limiting example, one or more of the treatments provided herein may reduce or effectively halt the oxalate accumulation in a subject. This attenuation may be exemplified by, for example, a decrease in one or more aspects (e.g., symptoms, tissue characteristics, and cellular etc.) of oxalate accumulation or symptoms resulting from such accumulation, no detectable progression (worsening) of one or more aspects of oxalate accumulation or symptoms resulting from such accumulation, or no detectable oxalate accumulation or symptoms resulting from such accumulation in a subject when they might otherwise be expected.

Complementary: As used herein, the term "complementary" refers to a structural relationship between two nucleotides (e.g., on two opposing nucleic acids or on opposing regions of a single nucleic acid strand) that permits the two nucleotides to form base pairs with one another. For example, a purine nucleotide of one nucleic acid that is complementary to a pyrimidine nucleotide of an opposing nucleic acid may base pair together by forming hydrogen bonds with one another. In some embodiments, complementary nucleotides can base pair in the Watson-Crick manner or in any other manner that allows for the formation of stable duplexes. In some embodiments, two nucleic acids may have regions of multiple nucleotides that are complementary with each other so as to form regions of complementarity, as described herein.

Deoxyribonucleotide: As used herein, the term "deoxyribonucleotide" refers to a nucleotide having a hydrogen in place of a hydroxyl at the 2' position of its pentose sugar as compared with a ribonucleotide. A modified deoxyribonucleotide is a deoxyribonucleotide having one or more modifications or substitutions of atoms other than at the 2' position, including modifications or substitutions in or of the sugar, phosphate group or base.

Double-stranded oligonucleotide: As used herein, the term "double-stranded oligonucleotide" refers to an oligonucleotide that is substantially in a duplex form. In some embodiments, complementary base-pairing of duplex region(s) of a double-stranded oligonucleotide is formed between antiparallel sequences of nucleotides of covalently separate nucleic acid strands. In some embodiments, complementary base-pairing of duplex region(s) of a double-stranded oligonucleotide is formed between antiparallel sequences of nucleotides of nucleic acid strands that are covalently linked. In some embodiments, complementary base-pairing of duplex region(s) of a double-stranded oligonucleotide is formed from a single nucleic acid strand that is folded (e.g., via a hairpin) to provide complementary antiparallel sequences of nucleotides that base pair together. In some embodiments, a double-stranded oligonucleotide comprises two covalently separate nucleic acid strands that are fully duplexed with one another. However, in some embodiments, a double-stranded oligonucleotide comprises two covalently separate nucleic acid strands that are partially duplexed, e.g., having overhangs at one or both ends. In some embodiments, a double-stranded oligonucleotide comprises antiparallel sequences of nucleotides that are partially complementary, and thus, may have one or more mismatches, which may include internal mismatches or end mismatches.

Duplex: As used herein, the term "duplex," in reference to nucleic acids (e.g., oligonucleotides), refers to a structure formed through complementary base-pairing of two antiparallel sequences of nucleotides.

Excipient: As used herein, the term "excipient" refers to a non-therapeutic agent that may be included in a composition, for example, to provide or contribute to a desired consistency or stabilizing effect.

Hepatocyte: As used herein, the term "hepatocyte" or "hepatocytes" refers to cells of the parenchymal tissues of the liver. These cells make up approximately 70-85% of the liver's mass and manufacture serum albumin, fibrinogen, and the prothrombin group of clotting factors (except for Factors 3 and 4). Markers for hepatocyte lineage cells may include, but are not limited to: transthyretin (Ttr), glutamine synthetase (Glu1), hepatocyte nuclear factor 1a (Hnf1a), and hepatocyte nuclear factor 4a (Hnf4a). Markers for mature hepatocytes may include, but are not limited to: cytochrome P450 (Cyp3a11), fumarylacetoacetate hydrolase (Fah), glucose 6-phosphate (G6p), albumin (Alb), and OC2-2F8. See, e.g., Huch et al., (2013), Nature, 494(7436): 247-250, the contents of which relating to hepatocyte markers is incorporated herein by reference.

Lactate dehydrogenase (LDH): As used herein the term "lactate dehydrogenase" or "LDH" refers to an enzyme that regulates the homeostasis of lactate/pyruvate, hydroxypyruvate/glycerate, and glyoxylate/oxalate metabolism. Functional LDH is composed of four monomeric polypeptide chains to form a tetramer. The two most common subunits, known as muscle (M) or heart (H) forms of LDH, are encoded by LDHA and LDHB genes, respectively. Five different isozymes have been identified based on their subunit composition (4H, 3H1M, 2H2M, 1H3M, 4M), which show similar enzymatic activities but different kinetic behaviors and tissue distributions. The major isozyme of liver and skeletal muscle, LDH5, has 4M subunits.

Lactate dehydrogenase A (LDHA): As used herein the term "lactate dehydrogenase A" or "LDHA" refers to a monomer of the LDH enzyme encoded by the LDHA gene (Entrez Gene ID: 3939), of which there exist at least five mRNA transcript variants (e.g., NCBI Reference Sequence: NM_005566.3, NM_001135239.1, NM_001165414.1, NM_001165415.1, and NM_001165416.1) encoding different isoforms.

Lactate dehydrogenase B (LDHB): As used herein the term "lactate dehydrogenase B" or "LDHB" refers to a monomer of the LDH enzyme encoded by the LDHB gene (Entrez Gene ID: 3945), of which there exist at least two mRNA transcript variants (e.g., NCBI Reference Sequence: NM_001174097.2 and NM_001315537.1) encoding different isoforms.

Loop: As used herein, the term "loop" refers to an unpaired region of a nucleic acid (e.g., oligonucleotide) that is flanked by two antiparallel regions of the nucleic acid that are sufficiently complementary to one another, such that under appropriate hybridization conditions (e.g., in a phosphate buffer, in a cells), the two antiparallel regions, which flank the unpaired region, hybridize to form a duplex (referred to as a "stem").

Modified Internucleotide Linkage: As used herein, the term "modified internucleotide linkage" refers to an internucleotide linkage having one or more chemical modifications compared with a reference internucleotide linkage comprising a phosphodiester bond. In some embodiments, a modified nucleotide is a non-naturally occurring linkage. In some embodiments, a modified internucleotide linkage confers one or more desirable properties to a nucleic acid in which the modified internucleotide linkage is present.

Modified Nucleotide: As used herein, the term "modified nucleotide" refers to a nucleotide having one or more chemical modifications compared with a corresponding reference nucleotide selected from: adenine ribonucleotide, guanine ribonucleotide, cytosine ribonucleotide, uracil ribonucleotide, adenine deoxyribonucleotide, guanine deoxyribonucleotide, cytosine deoxyribonucleotide and thymidine deoxyribonucleotide. In some embodiments, a modified nucleotide is a non-naturally occurring nucleotide. In some embodiments, a modified nucleotide has one or more chemical modifications in its sugar, nucleobase and/or phosphate group. In some embodiments, a modified nucleotide has one or more chemical moieties conjugated to a corresponding reference nucleotide. In some embodiments, a modified nucleotide provided herein may contribute to improved thermal stability, resistance to degradation, nuclease resistance, solubility, bioavailability, bioactivity, reduced immunogenicity, etc.

Nicked Tetraloop Structure: A "nicked tetraloop structure" is a structure of a RNAi oligonucleotide characterized by the presence of separate sense (passenger) and antisense (guide) strands, in which the sense strand has a region of complementarity with the antisense strand, and in which at least one of the strands, generally the sense strand, has a tetraloop configured to stabilize an adjacent stem region formed within the at least one strand.

Oligonucleotide: As used herein, the term "oligonucleotide" refers to a short nucleic acid, e.g., of less than 100 nucleotides in length. An oligonucleotide may be single-stranded or double-stranded. An oligonucleotide may or may not have duplex regions. As a set of non-limiting examples, an oligonucleotide may be, but is not limited to, a small interfering RNA (siRNA), microRNA (miRNA), short hairpin RNA (shRNA), dicer substrate interfering RNA (dsiRNA), antisense oligonucleotide, short siRNA, or single-stranded siRNA. In some embodiments, a double-stranded oligonucleotide is an RNAi oligonucleotide.

Overhang: As used herein, the term "overhang" refers to terminal non-base-pairing nucleotide(s) resulting from one strand or region extending beyond the terminus of a complementary strand with which the one strand or region forms a duplex. In some embodiments, an overhang comprises one or more unpaired nucleotides extending from a duplex region at the 5' terminus or 3' terminus of a double-stranded oligonucleotide. In certain embodiments, the overhang is a 3' or 5' overhang on the antisense strand or sense strand of a double-stranded oligonucleotide.

Phosphate analog: As used herein, the term "phosphate analog" refers to a chemical moiety that mimics the electrostatic and/or steric properties of a phosphate group. In some embodiments, an oligonucleotide has a phosphate analog at a 4'-carbon position of the sugar (referred to as a "4'-phosphate analog") at a 5'-terminal nucleotide. An example of a 4'-phosphate analog is oxymethylphosphonate, in which the oxygen atom of the oxymethyl group is bound to the sugar moiety (e.g., at its 4'-carbon) or analog thereof.

Reduced expression: As used herein, the term "reduced expression" of a gene refers to a decrease in the amount of RNA transcript or protein encoded by the gene and/or a decrease in the amount of activity of the gene in a cell or subject, as compared to an appropriate reference cell or subject. For example, the act of treating a cell with a double-stranded oligonucleotide (e.g., one having an antisense strand that is complementary to LDHA mRNA sequence) may result in a decrease in the amount of mRNA transcript, protein and/or enzymatic activity (e.g., encoded by the LDHA gene) compared to a cell that is not treated with the double-stranded oligonucleotide. Similarly, "reducing expression" as used herein refers to an act that results in reduced expression of a gene (e.g., LDHA).

Region of Complementarity: As used herein, the term "region of complementarity" refers to a sequence of nucleotides of a nucleic acid (e.g., a double-stranded oligonucleotide) that is sufficiently complementary to an antiparallel sequence of nucleotides to permit hybridization between the two sequences of nucleotides under appropriate hybridization conditions, e.g., in a phosphate buffer, in a cell, etc.

Ribonucleotide: As used herein, the term "ribonucleotide" refers to a nucleotide having a ribose as its pentose sugar, which contains a hydroxyl group at its 2' position. A modified ribonucleotide is a ribonucleotide having one or more modifications or substitutions of atoms other than at the 2' position, including modifications or substitutions in or of the ribose, phosphate group or base.

RNAi Oligonucleotide: As used herein, the term "RNAi oligonucleotide" refers to either (a) a double stranded oligonucleotide having a sense strand (passenger) and antisense strand (guide), in which the antisense strand or part of the antisense strand is used by the Argonaute 2 (Ago2) endonuclease in the cleavage of a target mRNA or (b) a single stranded oligonucleotide having a single antisense strand, where that antisense strand (or part of that antisense strand) is used by the Ago2 endonuclease in the cleavage of a target mRNA.

Strand: As used herein, the term "strand" refers to a single contiguous sequence of nucleotides linked together through internucleotide linkages (e.g., phosphodiester linkages, phosphorothioate linkages). In some embodiments, a strand has two free ends, e.g., a 5'-end and a 3'-end.

Subject: As used herein, the term "subject" means any mammal, including mice, rabbits, and humans. In one embodiment, the subject is a human or non-human primate. The terms "individual" or "patient" may be used interchangeably with "subject."

Synthetic: As used herein, the term "synthetic" refers to a nucleic acid or other molecule that is artificially synthesized (e.g., using a machine (e.g., a solid state nucleic acid synthesizer)) or that is otherwise not derived from a natural source (e.g., a cell or organism that normally produces the molecule.

Targeting ligand: As used herein, the term "targeting ligand" refers to a molecule (e.g., a carbohydrate, amino sugar, cholesterol, polypeptide or lipid) that selectively binds to a cognate molecule (e.g., a receptor) of a tissue or cell of interest and that is conjugatable to another substance for purposes of targeting the other substance to the tissue or cell of interest. In some embodiments, a targeting ligand comprises a GalNac moiety.

Tetraloop: As used herein, the term "tetraloop" refers to a loop that increases stability of an adjacent duplex formed by hybridization of flanking sequences of nucleotides. The increase in stability is detectable as an increase in melting temperature ($T_m$) of an adjacent stem duplex that is higher than the $T_m$ of the adjacent stem duplex expected, on average, from a set of loops of comparable length consisting of randomly selected sequences of nucleotides. For example, a tetraloop can confer a melting temperature of at least 50° C., at least 55° C., at least 56° C., at least 58° C., at least 60° C., at least 65° C. or at least 75° C. in 10 mM $NaHPO_4$ to a hairpin comprising a duplex of at least 2 base pairs in length. In some embodiments, a tetraloop may stabilize a base pair in an adjacent stem duplex by stacking interactions. In addition, interactions among the nucleotides in a tetraloop include but are not limited to non-Watson-Crick base-pairing, stacking interactions, hydrogen bonding, and contact interactions (Cheong et al., Nature 1990 Aug. 16; 346(6285):680-2; Heus and Pardi, Science 1991 Jul. 12; 253(5016):191-4). In some embodiments, a tetraloop comprises or consists of 3 to 6 nucleotides, and is typically 4 to 5 nucleotides. In certain embodiments, a tetraloop comprises or consists of three, four, five, or six nucleotides, which may or may not be modified (e.g., which may or may not be conjugated to a targeting moiety). In one embodiment, a tetraloop consists of four nucleotides. Standard IUPAC-IUB symbols may be used to refer to tetraloop nucleotides as described in Cornish-Bowden (1985) Nucl. Acids Res. 13: 3021-3030. For example, the letter "N" may be used to mean that any base may be in that position, the letter "R" may be used to show that A (adenine) or G (guanine) may be in that position, and "B" may be used to show that C (cytosine), G (guanine), or T (thymine) may be in that position. Examples of tetraloops include the UNCG family of tetraloops (e.g., UUCG), the GNRA family of tetraloops (e.g., GAAA), and the CUUG tetraloop (Woese et al., Proc Natl Acad Sci USA. 1990 November; 87(21):8467-71; Antao et al., Nucleic Acids Res. 1991 Nov. 11; 19(21):5901-5). Examples of DNA tetraloops include the d(GNNA) family of tetraloops (e.g., d(GTTA)), the d(GNRA) family of tetraloops, the d(GNAB) family of tetraloops, the d(CNNG) family of tetraloops, and the d(TNCG) family of tetraloops (e.g., d(TTCG)). See, for example: Nakano et al. Biochemistry, 41 (48), 14281-14292, 2002. SHINJI et al. Nippon Kagakkai Koen Yokoshu VOL. 78th; NO. 2; PAGE. 731 (2000), which are incorporated by reference herein for their relevant disclosures. In some embodiments, the tetraloop is contained within a nicked tetraloop structure.

Treat: As used herein, the term "treat" refers to the act of providing care to a subject in need thereof, e.g., through the administration a therapeutic agent (e.g., an oligonucleotide) to the subject, for purposes of improving the health and/or well-being of the subject with respect to an existing condition (e.g., a disease, disorder) or to prevent or decrease the likelihood of the occurrence of a condition. In some embodiments, treatment involves reducing the frequency or severity of at least one sign, symptom or contributing factor of a condition (e.g., disease, disorder) experienced by a subject.

II. Oligonucleotide-Based Inhibitors of LDHA Expression i. Oligonucleotide Sequence In some embodiments, an oligonucleotide described herein has a guide (antisense) strand having a sequence UCAGAUAAAAAGGACAACAUGG (SEQ ID NO: 1). In some embodiments, a sense strand is provided that forms a duplex with the antisense strand. In some embodiments, the sense strand comprises a stem-loop at its 3'-end. In certain embodiments, the sense strand comprises (e.g., at its 3'-end) a stem-loop set forth as: $S_1$-L-$S_2$, in which $S_1$ is complementary to $S_2$, and in which L forms a loop between $S_1$ and $S_2$ in a range of 2 to 6 nucleotides in length. In some embodiments, a duplex formed between $S_1$ and $S_2$ is 4, 5, 6, 7, or 8 base pairs in length. In some embodiments, a loop (L) of a stem-loop is a tetraloop (e.g., within a nicked tetraloop structure). A tetraloop may contain ribonucleotides, modified nucleotides, and/or combinations thereof. Typically, a tetraloop has 4 to 5 nucleotides. However, in some embodiments, a tetraloop comprises or consists of 3 to 6 nucleotides, and typically consists of 4 nucleotides. In certain embodiments, a tetraloop comprises or consists of three, four, five, or six nucleotides.

In some embodiments, the oligonucleotide described herein has a sense strand of sequence AUGUUGUCC-UUUUUAUCUGAGCAGCCGAAAGGCUGC (SEQ ID NO: 2). In one embodiment, the oligonucleotide comprises an antisense strand of sequence UCAGAUAAAAAGGACAACAUGG (SEQ ID NO: 1) and a sense strand of sequence (SEQ ID NO: 2)
AUGUUGUCCUUUUUAUCUGAGCAGCCGAAAGGCUGC.

ii. Oligonucleotide Modifications

In some embodiments, oligonucleotides of the present disclosure may include one or more suitable modifications. In some embodiments, a modified nucleotide has a modification in its base (or nucleobase), the sugar (e.g., ribose, deoxyribose), or the phosphate group. In certain embodiments of oligonucleotides provided herein, all or substantially all of the nucleotides of an oligonucleotide are modified. In certain embodiments, more than half of the nucleotides are modified. In certain embodiments, less than half of the nucleotides are modified.

a. Sugar Modifications

In some embodiments, a modified sugar (also referred to herein as a sugar analog) includes a modified deoxyribose or ribose moiety. In some embodiments, a nucleotide modification in a sugar comprises a 2'-modification. A 2'-modification may be 2'-aminoethyl, 2'-fluoro, 2'-O-methyl, 2'-O-methoxyethyl, or 2'-deoxy-2'-fluoro-β-d-arabinonucleic acid. Typically, the modification is 2'-fluoro or 2'-O-methyl. In some embodiments, a modification in a sugar comprises a modification of the sugar ring, which may comprise modification of one or more carbons of the sugar ring.

In some embodiments, one or more of the following positions are modified with a 2'-O-methyl: positions 1, 2, 4, 6, 7, 12, 14, 16, 18-26, or 31-36 of the sense strand and/or positions 1, 6, 8, 11-13, 15, 17, or 19-22 of the antisense strand. In certain embodiments, all of positions 1, 2, 4, 6, 7, 12, 14, 16, 18-26, and 31-36 of the sense strand and/or all of positions 1, 6, 8, 11-13, 15, 17, and 19-22 of the antisense strand are modified with a 2'-O-methyl. In some embodiments, one or more of the following positions are modified with a 2'-fluoro: positions 3, 5, 8-11, 13, 15, or 17 of the sense strand and/or positions 2-5, 7, 9, 10, 14, 16, or 18 of the antisense strand. In certain embodiments, all of positions 3, 5, 8-11, 13, 15, and 17 of the sense strand and/or all of positions 2-5, 7, 9, 10, 14, 16, and 18 of the antisense strand are modified with a 2'-fluoro.

In some embodiments, the terminal 3'-end group (e.g., a 3'-hydroxyl) is a phosphate group or other group, which can be used, for example, to attach linkers, adapters or labels.

b. 5' Terminal Phosphates

In some embodiments, 5'-terminal phosphate groups of oligonucleotides enhance the interaction with Argonaut 2. However, oligonucleotides comprising a 5'-phosphate group may be susceptible to degradation via phosphatases or other enzymes, which can limit their bioavailability in vivo. In some embodiments, oligonucleotides include analogs of 5' phosphates that are resistant to such degradation.

In some embodiments, an oligonucleotide has a phosphate analog at a 4'-carbon position of the sugar (referred to as a "4'-phosphate analog"). See, for example, International Application No. PCT/US2017/049909, entitled 4'-Phosphate Analogs and Oligonucleotides Comprising the Same, filed on Sep. 1, 2017, the contents of which relating to phosphate analogs are incorporated herein by reference.

In some embodiments, an oligonucleotide provided herein comprises a 4'-phosphate analog at a 5'-terminal nucleotide. In some embodiments, a phosphate analog is an oxymethylphosphonate, in which the oxygen atom of the oxymethyl group is bound to the sugar moiety (e.g., at its 4'-carbon) or analog thereof. In other embodiments, a 4'-phosphate analog is a thiomethylphosphonate or an aminomethylphosphonate, in which the sulfur atom of the thiomethyl group or the nitrogen atom of the aminomethyl group is bound to the 4'-carbon of the sugar moiety or analog thereof. In certain embodiments, a 4'-phosphate analog is an oxymethylphosphonate.

In certain embodiments, a phosphate analog attached to the oligonucleotide is a methoxy phosphonate (MOP). In certain embodiments, a phosphate analog attached to the oligonucleotide is a 5' mono-methyl protected MOP. In some embodiments, the following uridine nucleotide comprising a phosphate analog may be used, e.g., at the first position of a guide (antisense) strand:

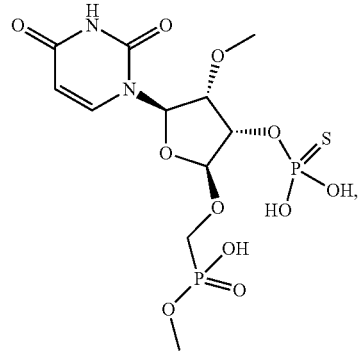 [SMILES: CO[C@@H]1[C@H](OP(O)(O)=S)[C@@H](OCP(=O)(O)OC)O[C@H]1n1ccc(=O)[nH]c1=O]

which modified nucleotide is referred to as [MePhosphonate-40-mU] or 5'-Methoxy, Phosphonate-4'oxy-2'-O-methyluridine.

c. Modified Internucleotide Linkages

In some embodiments, phosphate modifications or substitutions may result in an oligonucleotide that comprises at least one (e.g., at least 1, at least 2, at least 3 or at least 5) modified internucleotide linkage. In some embodiments, any one of the oligonucleotides disclosed herein comprises 1, 2, 3, 4, 5, 6, 7, 8, 9, or 10 modified internucleotide linkages. In some embodiments, at least one modified internucleotide linkage of any one of the oligonucleotides as disclosed herein is a phosphorothioate linkage.

In some embodiments, the oligonucleotide has a phosphorothioate linkage between one or more of: positions 1 and 2 of the sense strand, positions 1 and 2 of the antisense strand, positions 2 and 3 of the antisense strand, positions 3 and 4 of the antisense strand, positions 20 and 21 of the antisense strand, and positions 21 and 22 of the antisense strand. In certain embodiments, the oligonucleotide has a phosphorothioate linkage between each of: positions 1 and 2 of the sense strand, positions 1 and 2 of the antisense strand, positions 2 and 3 of the antisense strand, positions 3 and 4 of the antisense strand, positions 20 and 21 of the antisense strand, and positions 21 and 22 of the antisense strand.

iii. Targeting Ligands

In some embodiments, oligonucleotides disclosed herein are modified to facilitate targeting of a particular tissue, cell or organ, e.g., to facilitate delivery of the oligonucleotide to the liver. In certain embodiments, oligonucleotides disclosed herein may be modified to facilitate delivery of the oligonucleotide to the hepatocytes of the liver.

In some embodiments, an oligonucleotide comprises a nucleotide that is conjugated to one or more targeting ligands. In certain embodiments, the targeting ligand is one or more GalNAc moieties. GalNAc is a high affinity ligand for asialoglycoprotein receptor (ASGPR), which is primarily expressed on the sinusoidal surface of hepatocyte cells and has a major role in binding, internalization, and subsequent clearance of circulating glycoproteins that contain terminal galactose or N-acetylgalactosamine residues (asialoglycoproteins). In some embodiments, conjugation of GalNAc moieties to oligonucleotides of the instant disclosure is used to target these oligonucleotides to the ASGPR expressed on these hepatocyte cells. In some embodiments, an oligonucleotide of the instant disclosure is conjugated directly or indirectly to a monovalent GalNAc moiety. In some embodiments, an oligonucleotide of the instant disclosure is conjugated to one or more bivalent GalNAc, trivalent GalNAc, or tetravalent GalNAc moieties.

In some embodiments, an oligonucleotide herein comprises a monovalent GalNac attached to a Guanidine nucleotide, referred to as [ademG-GalNAc] or 2'-aminodiethoxymethanol-Guanidine-GalNAc, as depicted below:

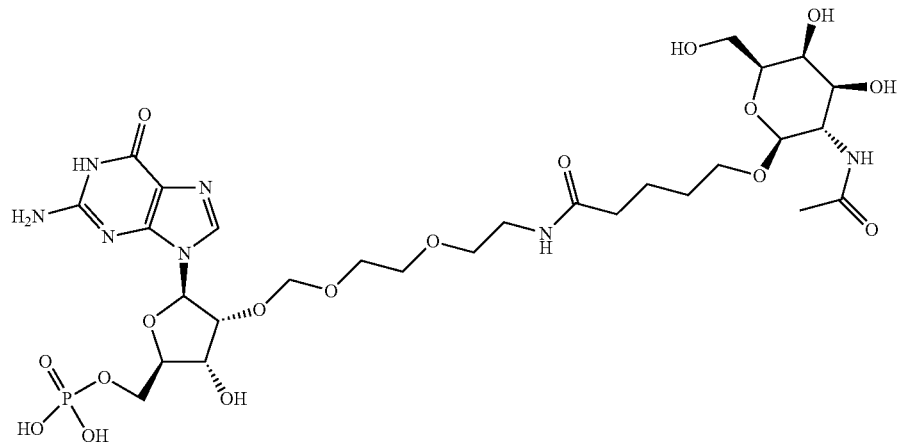 [SMILES: CC(=O)N[C@@H]1[C@@H](OCCCCC(=O)NCCOCCOCO[C@@H]2[C@H](O)[C@@H](COP(=O)(O)O)O[C@H]2n2cnc3c(=O)[nH]c(N)nc32)O[C@@H](CO)[C@@H](O)[C@H]1O]

In some embodiments, an oligonucleotide herein comprises a monovalent GalNac attached to an adenine nucleotide, referred to as [ademA-GalNAc] or 2'-aminodiethoxymethanol-Adenine-GalNAc, as depicted below.

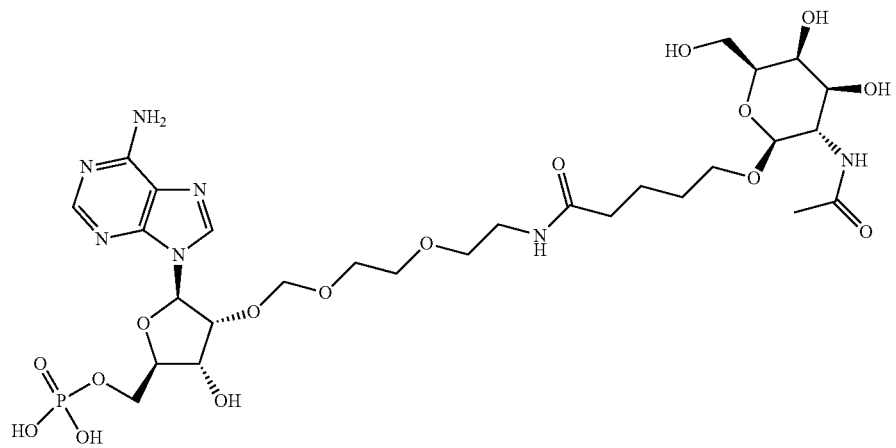 [SMILES: CC(=O)N[C@@H]1[C@@H](OCCCCC(=O)NCCOCCOCO[C@@H]2[C@H](O)[C@@H](COP(=O)(O)O)O[C@H]2n2cnc3c(N)ncnc32)O[C@@H](CO)[C@@H](O)[C@H]1O]

In some embodiments, 2 to 4 nucleotides of an oligonucleotide are each conjugated to a GalNAc moiety. In some embodiments, 2 to 4 nucleotides of the loop (L) of the stem-loop are each conjugated to a separate GalNAc. For example, an oligonucleotide may comprise a stem-loop at the 3' end of the sense strand and all four nucleotides of the loop may be individually conjugated to a monovalent GalNAc moiety. An example of such conjugation is shown below for a loop comprising from 5' to 3' the nucleotide sequence GAAA (L=linker, X=heteroatom) stem attachment points are shown. Such a loop may be present, for example, at positions 27-30 of the molecule shown in FIG. 1A. In the chemical formula,

is an attachment point to the oligonucleotide strand.

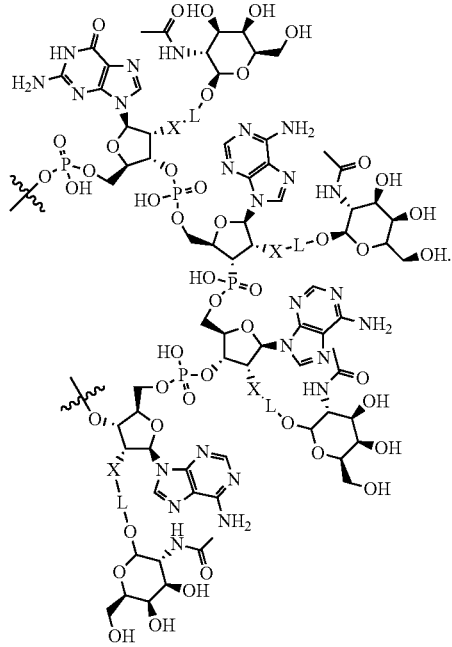

Appropriate methods or chemistry (e.g., click chemistry) may be used to link a targeting ligand to a nucleotide. In some embodiments, the linker is a labile linker. However, in other embodiments, the linker is more stable. In some embodiments, a targeting ligand is conjugated to a nucleotide using a click linker. In some embodiments, an acetal-based linker is used to conjugate a targeting ligand to a nucleotide of an oligonucleotide described herein. Acetal-based linkers are disclosed, for example, in International Patent Application Publication Number WO2016100401 A1, which published on Jun. 23, 2016, and the contents of which relating to such linkers are incorporated herein by reference.

An example is shown below for a loop comprising from 5' to 3' the nucleotides GAAA, in which GalNac moieties are attached to nucleotides of the loop using an acetal linker. Such a loop may be present, for example, at positions 27-30 of the molecule shown in FIG. 1A. In the chemical formula,

is an attachment point to the oligonucleotide strand.

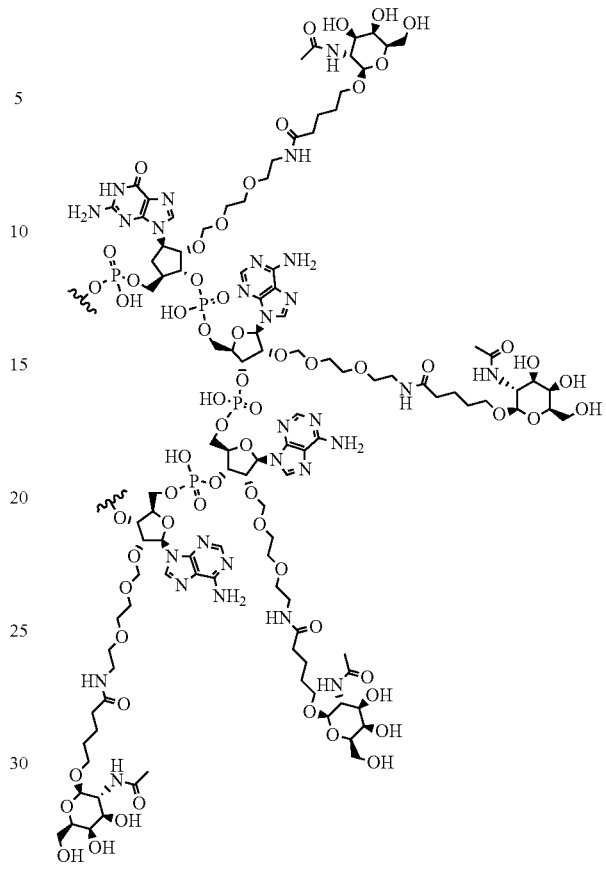

III. Formulations

Formulations are provided herein to facilitate oligonucleotide use. For example, provided herein are compositions comprising oligonucleotides for use in reducing the expression of LDHA. Such compositions can be suitably formulated such that when administered to a subject, either into the immediate environment of a target cell or systemically, a sufficient portion of the oligonucleotides enter the cell to reduce LDHA expression. In some embodiments, oligonucleotide formulations can be used to deliver oligonucleotides for the reduction of LDHA as disclosed herein. In some embodiments, formulations as disclosed herein comprise an excipient.

In some embodiments, a pharmaceutical composition is formulated to be compatible with its intended route of administration. Examples of routes of administration include, but are not limited to, subcutaneous, intradermal, transmucosal, intravenous, and rectal administration.

IV. Methods of Use i. Reducing LDHA Expression in Cells

In some embodiments, methods are provided for delivering to a cell an effective amount any one of oligonucleotides disclosed herein for purposes of reducing expression of LDHA in the cell. Methods provided herein are useful in any appropriate cell type. In some embodiments, a cell is any cell that expresses LDHA. In some embodiments, a cell to which the oligonucleotide is delivered is ex vivo or in vitro (i.e., can be delivered to a cell in culture or to an organism in which the cell resides). In specific embodiments, methods are provided for delivering to a cell an effective amount any one of the oligonucleotides disclosed herein for purposes of reducing expression of LDHA in hepatocytes.

The consequences of inhibition can be confirmed by an appropriate assay to evaluate one or more properties of a cell or subject, or by biochemical techniques that evaluate molecules indicative of LDHA expression (e.g., RNA, protein, enzyme activity, metabolite levels, oxalate levels, etc.). In some embodiments, the extent to which an oligonucleotide provided herein reduces levels of expression of LDHA is evaluated by comparing expression levels (e.g., mRNA or protein levels of LDHA to an appropriate control (e.g., a level of LDHA expression in a cell or population of cells to which an oligonucleotide has not been delivered or to which a negative control has been delivered). In some embodiments, an appropriate control level of LDHA expression may be a predetermined level or value, such that a control level need not be measured every time. The predetermined level or value can take a variety of forms. In some embodiments, a predetermined level or value can be single cut-off value, such as a median or mean.

In some embodiments, administration of an oligonucleotide as described herein results in a reduction in the level of LDHA expression in a cell. In some embodiments, the reduction in levels of LDHA expression may be a reduction to 1% or lower, 5% or lower, 10% or lower, 15% or lower, 20% or lower, 25% or lower, 30% or lower, 35% or lower, 40% or lower, 45% or lower, 50% or lower, 55% or lower, 60% or lower, 70% or lower, 80% or lower, or 90% or lower compared with an appropriate control level of LDHA. The appropriate control level may be a level of LDHA expression in a cell or population of cells that has not been contacted with an oligonucleotide as described herein. In some embodiments, the effect of delivery of an oligonucleotide to a cell according to a method disclosed herein is assessed after a finite period of time. For example, levels of LDHA may be analyzed in a cell at least 8 hours, 12 hours, 18 hours, 24 hours; or at least one, two, three, four, five, six, seven, fourteen, twenty-one, twenty-eight, thirty-five or more days after introduction of the oligonucleotide into the cell.

ii. Treatment Methods

In some embodiments, RNAi oligonucleotides disclosed herein are useful for reducing hepatic oxalate production in a subject, e.g., a patient having a primary hyperoxaluria. In some embodiments, RNAi oligonucleotides disclosed herein are useful for reducing urine oxalate levels. In some embodiments, RNAi oligonucleotides disclosed herein are useful for treating primary hyperoxaluria, including PH1, PH2 and/or PH3, as well as idiopathic hyperoxaluria. Accordingly, aspects of the disclosure relate to methods for reducing LDHA expression in for treatment of oxalate accumulation. In some aspects, methods are provided for treating a primary hyperoxaluria, including PH1, PH2 and/or PH3, as well as idiopathic hyperoxaluria. In some embodiments, the methods may comprise administering to a subject in need thereof an effective amount of any one of the oligonucleotides disclosed herein. Such treatments could be used, for example, to attenuate or halt oxalate accumulation. The present disclosure provides for both prophylactic and therapeutic methods of treating a subject at risk of (or susceptible to) a disease or disorder associated with oxalate accumulation.

In some embodiments, the subject to be treated is a subject who will benefit therapeutically from a reduction in the accumulation of oxalate, e.g., in the liver. In some embodiments, the subject to be treated is a subject having or suspected of having a condition resulting in oxalate accumulation, kidney disease, or a primary hyperoxaluria, including PH1, PH2 and/or PH3, as well as idiopathic hyperoxaluria.

Methods described herein typically involve administering to a subject an effective amount of an oligonucleotide, that is, an amount capable of producing a desirable therapeutic result. A therapeutically acceptable amount may be an amount that is capable of treating a disease or disorder. The appropriate dosage for any one subject will depend on certain factors, including the subject's size, body surface area, age, the particular composition to be administered, the active ingredient(s) in the composition, time and route of administration, general health, and other drugs being administered concurrently. Typically, oligonucleotides disclosed herein are administered intravenously or subcutaneously.

As a non-limiting set of examples, the oligonucleotides of the instant disclosure would typically be administered quarterly (once every three months), bi-monthly (once every two months), monthly, or weekly. For example, the oligonucleotides may be administered every one, two, or three weeks. The oligonucleotides may be administered monthly in some embodiments.

In some embodiments, the subject to be treated is a human. In some embodiments, the subject to be treated is a non-human primate or other mammalian subject (e.g., a mouse or rat). In some embodiments, the subject to be treated is a non-human primate or other mammalian subject engineered to express a human LDHA transcript (e.g., from an AAV delivered expression vector).

EXAMPLES

Example 1: Specific RNAi Oligonucleotide Useful in Specific Knockdown of LDHA

Figure 1B:
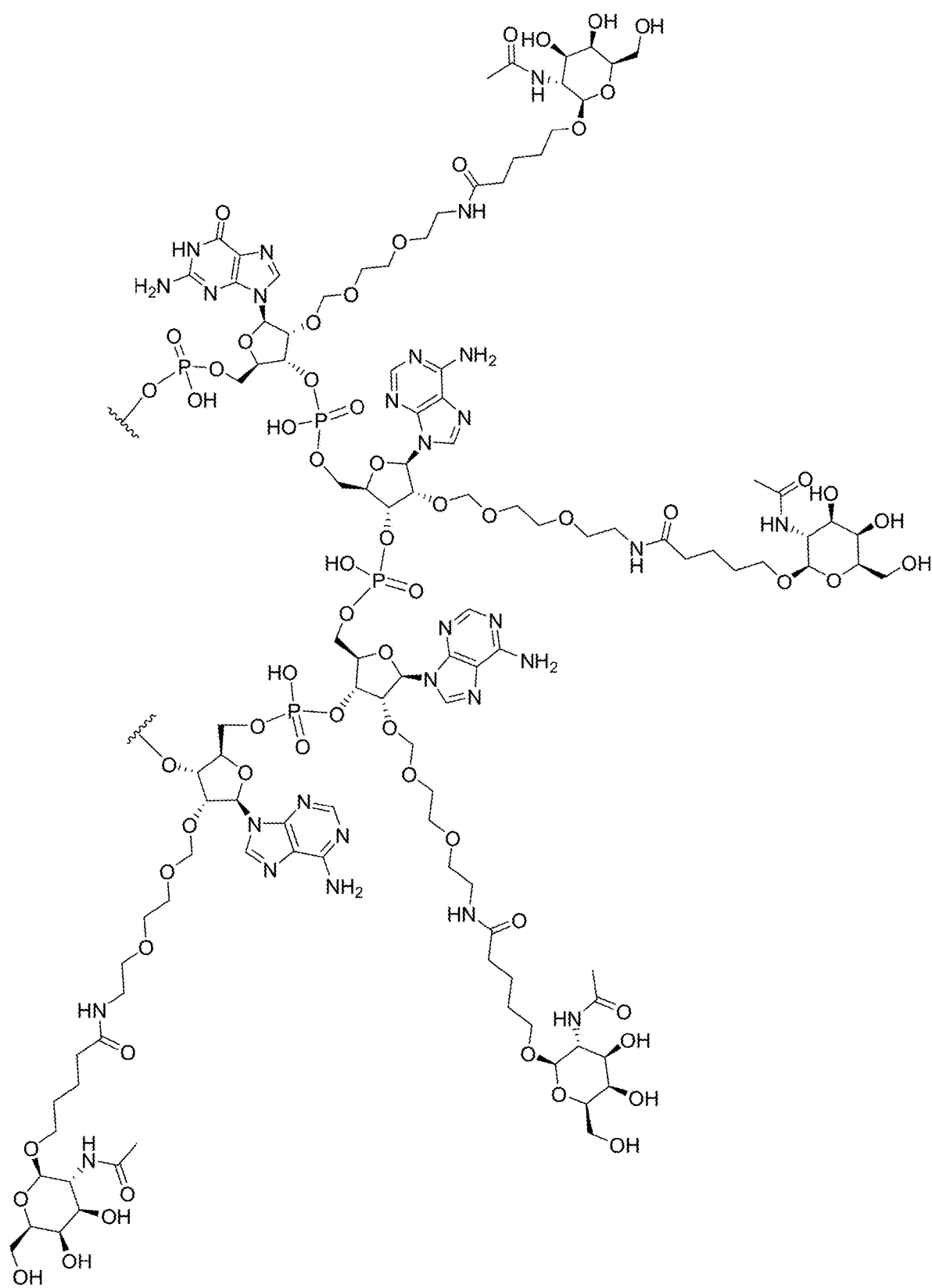
FIG. 1B is a non-limiting representation of a chemical structure of an example of a loop sequence present at positions 27-30 of the passenger (sense) strand shown in FIG. 1A.
Figure 1C:
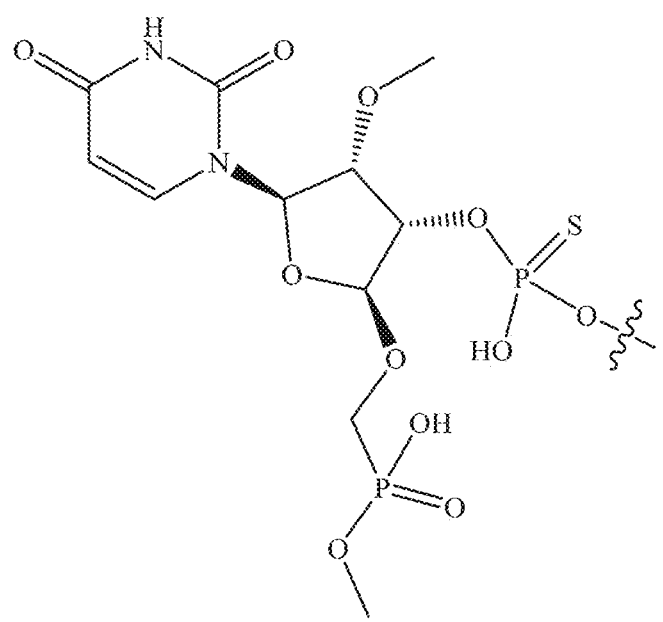
FIG. 1C is a non-limiting representation of a chemical structure of the modified uridine shown at position 1 of the guide (antisense) strand shown in FIG. 1A. In the chemical formula, === or === is a single bond in which the stereochemistry of the moieties immediately attached thereto is not specified.
Figure 2A:
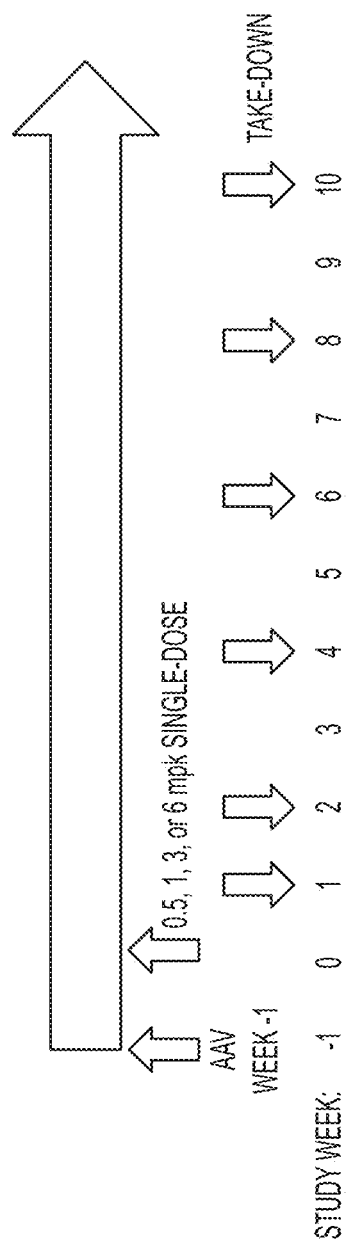
FIG. 2A is a schematic showing a timeline for in vivo evaluation of the specific oligonucleotide shown in FIG. 1A using a LDHA AAV mouse model. AAV injection was performed at week −1, and single doses of the oligonucleotide were injected subcutaneously at 0.5, 1, 3, or 6 mg/kg as shown. At 1, 2, 4, 6, 8, and 10 weeks a 4 mm biopsy punch was collected and flash-frozen in a block and in RNAlater for mRNA knockdown analyses.
Figure 3:
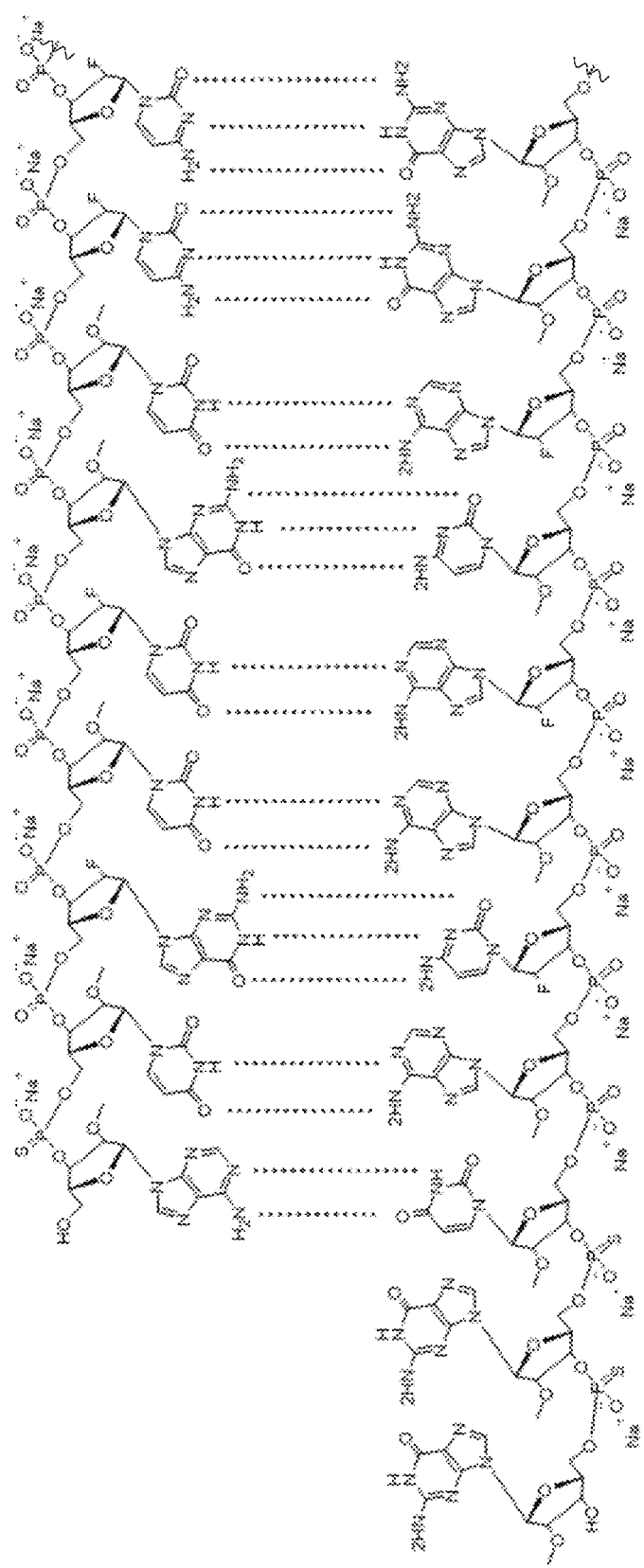
FIG. 3 is a non-limiting chemical structure of an RNAi oligonucleotide having a guide (antisense) strand with a region of complementarity with LDHA mRNA and a passenger (sense) strand having a nicked tetraloop structure.

An RNAi oligonucleotide having an antisense strand of sequence UCAGAUAAAAAGGACAACAUGG (SEQ ID NO: 1) and a sense strand of sequence AUGUUGUCC-UUUUUAUCUGAGCAGCCGAAAGGCUGC (SEQ ID NO: 2) was evaluated for its ability to knockdown LDHA mRNA expression. In the RNAi oligonucleotide, the following positions are modified with a 2'-O-methyl (shown as 2'-OMe): positions 1, 2, 4, 6, 7, 12, 14, 16, 18-26, and 31-36 of the sense strand and positions 1, 6, 8, 11-13, 15, 17, and 19-22 of the antisense strand. The following positions are modified with a 2'-fluoro (shown as 2'-F): positions 3, 5, 8-11, 13, 15, or 17 of the sense strand and positions 2-5, 7, 9, 10, 14, 16, and 18 of the antisense strand. The RNAi oligonucleotide has a phosphorothioate linkage between each of: positions 1 and 2 of the sense strand, positions 1 and 2 of the antisense strand, positions 2 and 3 of the antisense strand, positions 3 and 4 of the antisense strand, positions 20 and 21 of the antisense strand, and positions 21 and 22 of the antisense strand. FIG. 1B is a representation of the chemical structure of positions 27-30 of the passenger (sense) strand shown in FIG. 1A and FIG. 1C is a representation of the chemical structure of the modified uridine shown at position 1 of the guide (antisense) strand in the same molecule. FIG. 3 is a chemical structure of the RNAi oligonucleotide. An RNAi oligonucleotide of this chemical structure has been referred to as LDHA-1. GalNAc sugars are conjugated to the nucleotides that comprise positions 27 to 30 on the sense strand. The dose response and duration of knockdown of LDHA mRNA by LDHA-1 in the livers of healthy female mice was evaluated in vivo using a human LDHA AAV mouse model. Human LDHA mRNA was expressed under control of the thyroid hormone-binding globulin promoter through AAV9 virus transduction. To establish a mouse model, female CD-1 mice of 4-6 weeks old were dosed intravenously (IV) with a controlled titer of AAV9 virus to generate stable human LDHA mRNA expression. FIG. 2A is a schematic showing the timeline of this evaluation. The AAV injection (at a dosage of $7.5 \times 10^{11}$ genomic copies in 100 μL) occurred at week −1, and single doses of LDHA-1 were injected subcutaneously one week later at 0.5 mg/kg (n=20 mice), 1 mg/kg (n=30 mice), 3 mg/kg (n=30 mice), or 6 mg/kg (n=30 mice) as shown. At 1, 2, 4, 6, 8, and 10 weeks a 4 mm liver biopsy punch was collected and flash-frozen in a block and in RNAlater (ThermoFisher Scientific) for mRNA knockdown analyses.

Figure 2B:
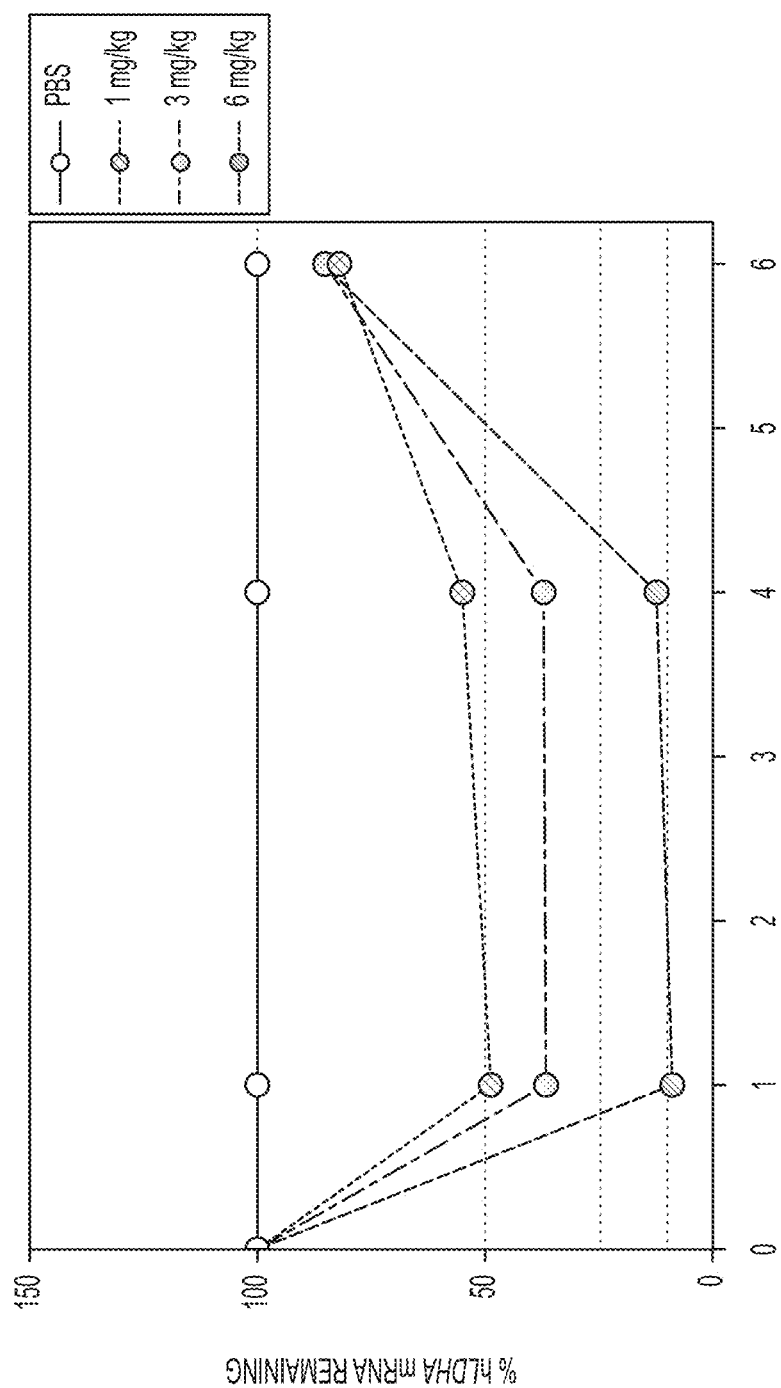
FIG. 2B is a graph demonstrating a subset of the results of the study described in Example 1. The percentage of hLDHA mRNA remaining is shown in the weeks post-dose after 1, 3, or 6 mg/kg doses. These results were normalized to time-matched PBS. Dose-dependent reduction of human LDHA mRNA was sustained for four weeks post-dose.

FIG. 2B is a graph demonstrating a subset of the results of the study described in FIG. 2A. The percentage of hLDHA mRNA remaining is shown in the weeks post-dose for the 1, 3, or 6 mg/kg doses. These results were normalized to time-matched PBS (n=40 mice). The results show that rapid and sustained knockdown of ectopically expressed LDHA mRNA was achieved after a single SC dose of 1, 3, or 6 mg/kg of LDHA-1 in healthy mice expressing human LDHA.

A single SC dose of 6 mg/kg of LDHA-1 reduced human LDHA mRNA expression in the liver by 90% compared to the PBS control one week post-dose (p≤0.05). Dose-dependent reduction of human LDHA mRNA was sustained for four weeks post-single dose. LDHA expression was recovered 6 weeks post single-dose.

A single SC dose of 3 mg/kg of LDHA-1 reduced human LDHA mRNA expression in the liver by 63% compared to the PBS control one week post-dose. The degree of human LDHA mRNA knockdown remained constant for four weeks post-single dose with recovery of baseline LDHA expression 6 weeks post single-dose.

A single SC dose of 1 mg/kg of LDHA-1 reduced human LDHA mRNA expression in the liver by 50% compared to the PBS control one week post-dose. The degree of human LDHA mRNA knockdown was sustained with 45% knockdown four weeks post-dose. LDHA mRNA expression returned to baseline by 6 weeks post single-dose.

Materials and Methods for Example 1

Animals: Female CD-1 mice, (date of birth Aug. 9, 2016, date of receipt Sep. 13, 2016), were purchased from Charles River Laboratories (Kingston, N.Y., Strain Code 022). Mice were allowed to acclimate for at least 3 days before start of dosing. Mice were kept under specific pathogen-free husbandry conditions, with access to laboratory chow and water ad libitum.

RNAi Oligonucleotide LDHA-1: a chemically synthesized double-stranded duplex RNA oligonucleotide with GalNAc functionality in sterile phosphate-buffered saline (PBS). The oligonucleotides were stored at −20° C. Before use, the oligonucleotides were thawed and mixed well (gentle vortexing) then equilibrated to room temperature for at least 30 minutes.

LDHA mRNA Measurement by RT-qPCR: Approximately 50 mg of sample was homogenized in 0.75 mL phenol/guanidine-based QIAzol Lysis Reagent (Qiagen, Valencia, Calif.) using a Tissuelyser II (Qiagen, Valencia, Calif.). The homogenate was extracted with 1-Bromo-3-chloropropane (Sigma-Aldrich, St. Louis, Mo.). RNA was extracted from 0.2 ml of the aqueous phase using the MagMax Technology (ThermoFisher Scientific, Waltham, Mass.) according to the manufacturer's instructions. RNA was quantified using spectrometry at 260 and 280 nm. RT-qPCR assays from Integrated DNA Technologies (Coralville, Iowa) and reagents from ThermoFisher Scientific (Waltham, Mass.) and BioRad Laboratories (Hercules, Calif.) were used to measure LDHA mRNA level with normalization to AA V9 plasmid levels. The degree of LDHA mRNA reduction in the LDHA-1 treatment groups was calculated as the percent of expression (normalized to AAV9 plasmid copy numbers determined by qPCR of DNA) relative to the average expression level of the PBS control group on the same day, where LDHA mRNA expression in the PBS control group was set at 100%. Graphs were generated in and data were analyzed using GraphPad Prism. One-way analysis of variance (ANOVA) using Dunnett's multiple comparisons test was performed to compare LDHA mRNA levels (normalized to AAV9 copy numbers) in LDHA-1-treated groups relative to the PBS control group of the same time point.

Example 2: Toxicity and Toxicokinetic Study of LDHA-1 Targeting LDHA in Juvenile and Young Adult Cynomolgus Monkeys A 5-week repeat-dose subcutaneous toxicity and toxicokinetic study was designed to demonstrate the effect of the LDHA-targeting oligonucleotides in juvenile and young adult cynomolgus monkeys given two subcutaneous administrations of 30, 100, or 300 mg/kg of the LDHA-1 described in Example 1 (see also FIG. 3). Male and female, juvenile and young adult cynomolgus monkeys received subcutaneous (SC) injections of 0 (sterile water for injection, SWFI on Day 1, sterile saline on Day 29), 30, 100, or 300 mg/kg LDHA-1 on Days 1 and 29. Liver tissue was collected at terminal sacrifice (Day 31) and recovery sacrifice (Day 57) for analysis of LDHA mRNA levels by RT-qPCR, LDH protein levels by western analysis, and LDH activity by enzymatic assay.

The study design is shown in Table 1. Liver tissues were collected from cynomolgus monkeys at terminal sacrifice (Day 31) and recovery sacrifice (Day 57) and were either flash frozen in liquid nitrogen for western blot and LDH activity assay, or incubated in RNAlater and frozen for RT-qPCR analysis.

Figure 4:
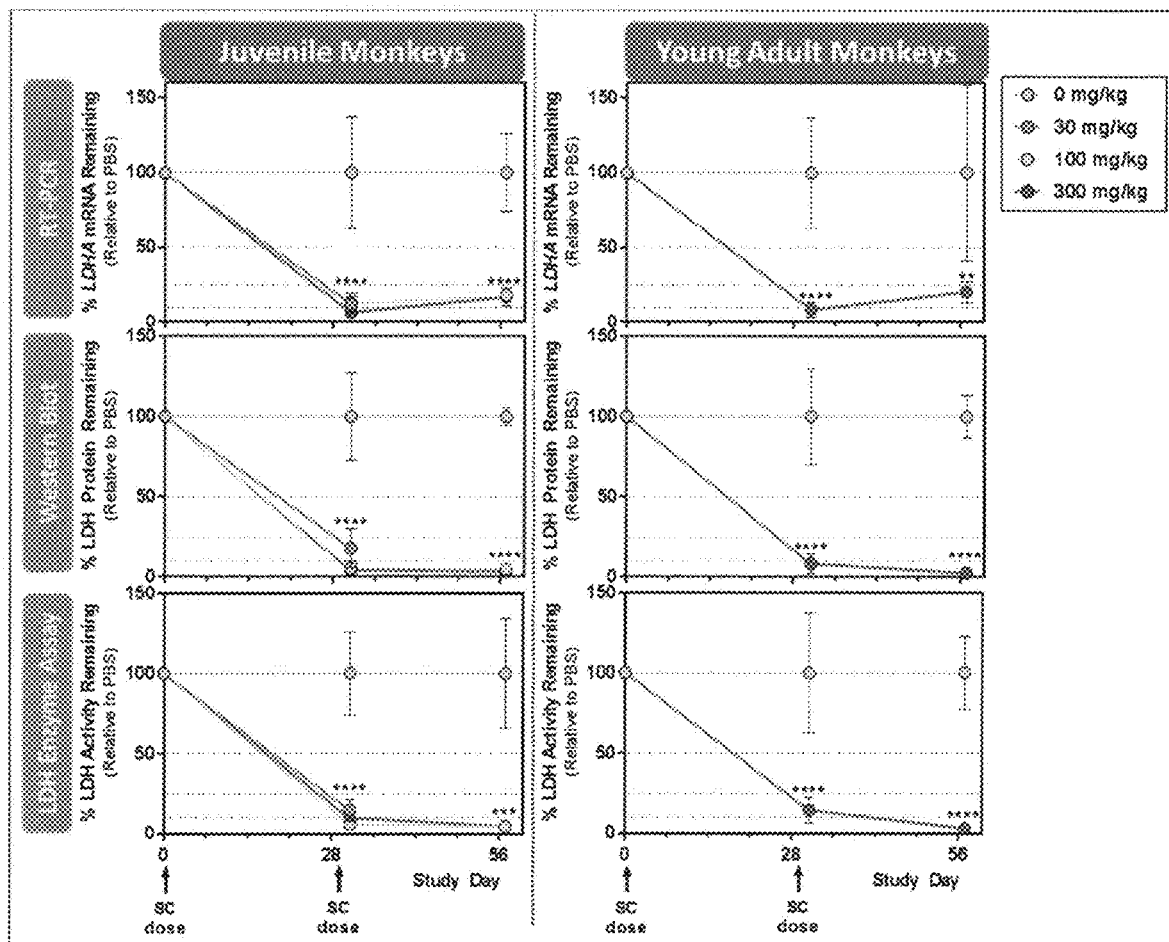
FIG. 4 is a graph showing the reduction of LDHA mRNA (upper panels), LDH protein (middle panels), and LDH activity (% Remaining, lower panels) after two doses of the oligonucleotide as shown in FIG. 3 in Cynomolgus Monkeys (juvenile and young adult) on days 28 and 56 after first dose.
Figure 5:
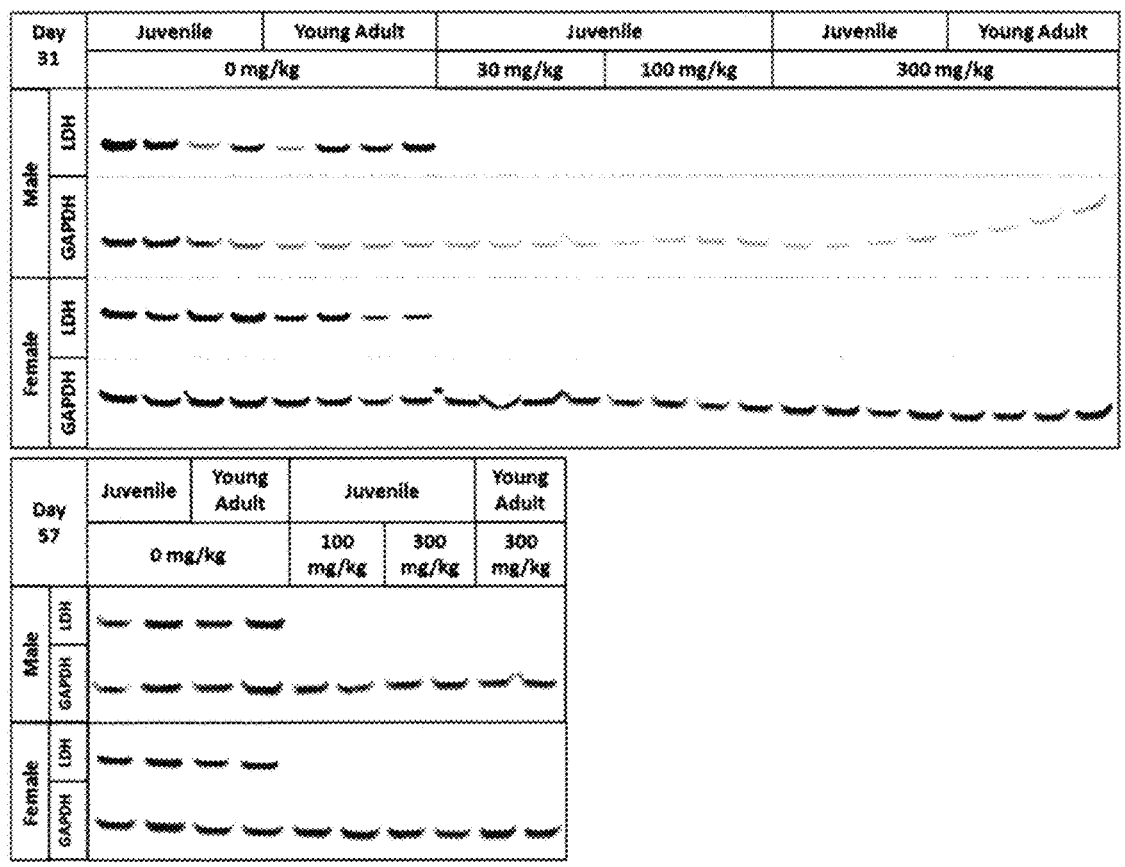
FIG. 5 is a graph showing the reduction of LDH protein levels (as detected by western blot) after two doses of the oligonucleotide as shown in FIG. 3 in Cynomolgus Monkeys.

After administration of a two doses of 30, 100, or 300 mg/kg LDHA-1, monkey LDHA mRNA expression, LDH protein concentrations, and LDH activity were all reduced significantly at the terminal sacrifice on Day 31 (p≤0.0001) at all dose levels with no apparent dose response. Similar findings were seen at the recovery sacrifice on Day 57 (p<0.0001, p≤0.001, p≤0.01 as indicated, statistical significance calculated using an unpaired t test); no recovery of the knockdown of LDHA mRNA, LDH protein, and LDH activity was observed (FIG. 4). The effects of dose on hepatic LDH protein levels as measured by western blot are shown in FIG. 5. LDH protein levels were notably reduced at all dose levels at both the terminal sacrifice (Day 31) and recovery sacrifice (Day 57).

The result showed that on Day 31, LDHA-1 displayed potent activity in reducing monkey LDHA mRNA expression, LDH protein concentrations, and LDH activity at all dose levels compared with controls with no apparent dose response. The reduction persisted until Day 57 with no recovery of target knockdown evident.

TABLE 1

Study design of toxicity and toxicokinetic study

| | | Dose | | | Number of Animals | |
|---|---|---|---|---|---|---|
| | | Level | Concentration | Volume[a] | | |
| Group | Age | (mg/kg) | (mg/ml) | (ml/kg) | Males | Females |
| 1 | Juvenile | 0 | 0 | 1.5 | $4^b + 2^c$ | $4^b + 2^c$ |
| 2 | Young Adule | 0 | 0 | 1.5 | $4^b + 2^c$ | $4^b + 2^c$ |
| 3 | Juvenile | 30 | 200 | 0.15 | $4^b$ | $4^b$ |
| 4 | Juvenile | 100 | 200 | 0.5 | $4^b + 2^c$ | $4^b + 2^c$ |
| 5 | Juvenile | 300 | 200 | 1.5 | $4^b + 2^c$ | $4^b + 2^c$ |
| 6 | Young Adule | 300 | 200 | 1.5 | $4^b + 2^c$ | $4^b + 2^c$ |

[a]total dose volume will be calculated based on the most recent body weight
[b]Terminal necropsy on day 31
[c]recovery necropsy on day 57

In addition, a 39-week repeat-dose subcutaneous toxicity and toxicokinetic study of LDHA-targeting oligonucleotides was carried out in juvenile and young adult cynomolgus monkeys given ten SC administrations of 30, 100, or 300 mg/kg LDHA-1 described in Example 1 to evaluate the reduction of LDHA mRNA levels and to quantitate the concentration of LDHA-1 incorporated into the RNA-induced silencing complex (RISC). Juvenile monkeys received subcutaneous (SC) injections of 0 (saline), 30, 100, or 300 mg/kg of LDHA-1 and young-adult monkeys received SC injections of 0 (saline) or 300 mg/kg LDHA-1 on study Days 1, 29, 57, 85, 113, 141, 169, 197, 225, and 253. Liver tissue was collected at terminal sacrifice (Day 255, 2 days after the last dose) and recovery sacrifice (Day 309, 8 weeks after the last dose) for analysis of LDHA mRNA levels by RT-qPCR. Liver samples collected at Day 255 were also used to quantitate the concentration of LDHA-1 incorporated into the RNA-induced silencing complex (RISC), measured by Argonaute protein 2 (Ago2) immunoprecipitation followed by Stem-Loop (SL)-RT-qPCR.

Figure 6:
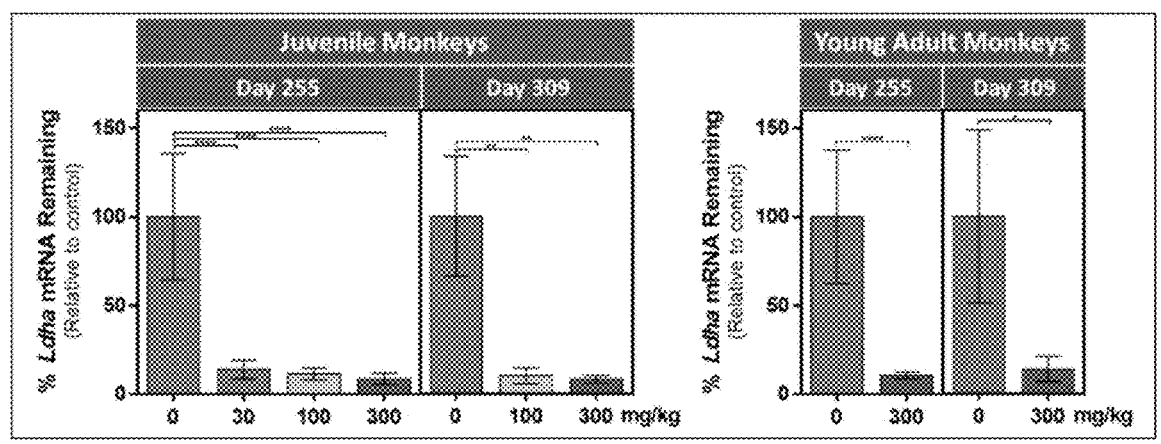
FIG. 6 is a graph showing the reduction of LDHA mRNA expression (% Remaining) after ten doses of the oligonucleotide as shown in FIG. 3 in cynomolgus monkeys.

Potent pharmacodynamic activity of LDHA-1 was evident at the end of the dosing period (Day 255). Monkey LDHA mRNA expression was reduced (91.4% to 86.1% reduction, P≤0.0001) at all dose levels. The concentration of LDHA-1 loaded into the RISC complex was dose related with significantly higher concentrations at a dose level of 300 mg/kg (5.6 ng/g) compared with 30 mg/kg (2.1 ng/g) (P≤0.05). The pharmacodynamic effects of LDHA-1, as indicated by significant reduction (92.0% to 86.2%) of LDHA mRNA expression, persisted for at least 8 weeks post dose with no recovery observed (FIG. 6). Determination of LDHA mRNA reduction at Day 309 was deemed sufficient for assessment of pharmacodynamic recovery, thus concentrations of LDHA-1 loaded into the RISC complex at Day 309 were not assessed.

Figure 7:
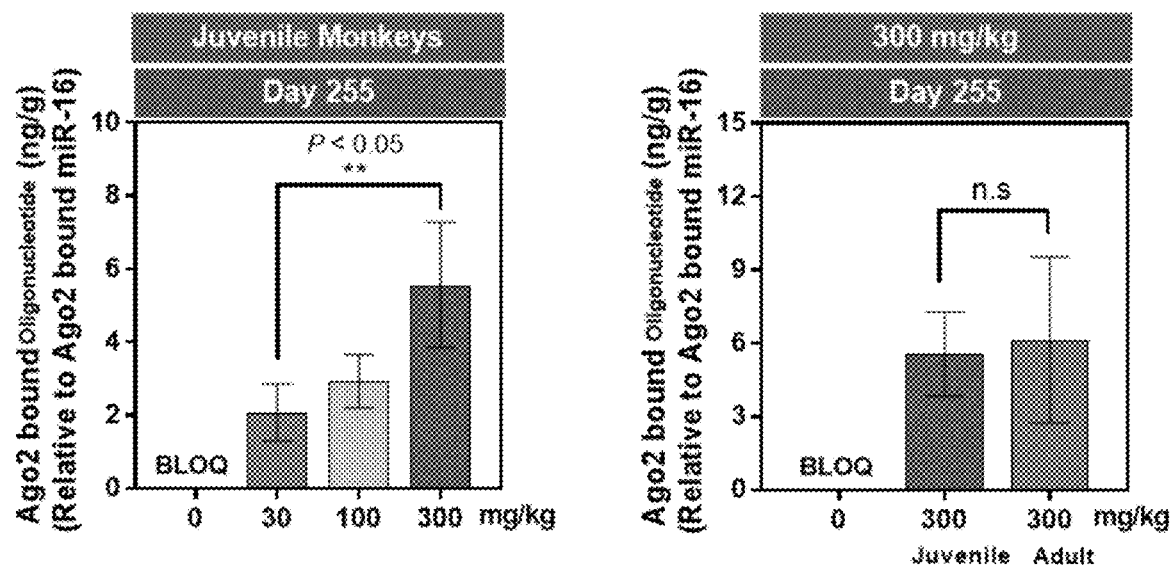
FIG. 7 is a graph showing the concentrations of the oligonucleotide incorporated in Ago2/RISC after ten doses of the oligonucleotide as shown in FIG. 3 in cynomolgus monkeys.

Quantification of LDHA-1 incorporated in RISC at Study Day 255 is reported in FIG. 7. Graphical representation of mean±SD for each dose group. On Day 255, RISC-incorporated LDHA-1 concentrations in the liver increased with increasing dose. LDHA-1 concentrations were increased significantly (P<0.05 at the 300 mg/kg dose compared with the 30 mg/kg dose. The concentrations of LDHA-1 incorporated in the RISC complex was comparable between juvenile and young-adult monkeys dosed at 300 mg/kg.

Potent pharmacodynamic activity of LDHA-1 was evident at the end of the dosing period (Day 255). Monkey LDHA mRNA expression was reduced at all dose levels compared with controls. In contrast, the concentration of LDHA-1 incorporated into the RISC complex was dose related, with significantly higher concentrations at a dose level of 300 mg/kg compared with 30 mg/kg. The pharmacodynamic effects of LDHA-1, as measured by reduction in LDHA mRNA, persisted until Day 309 (8 weeks post dose) with no recovery evident.

Materials and Methods for Example 2

LDHA mRNA Measurement by RT-qPCR: Approximately 50 mg of each sample was homogenized in 0.75 mL phenol/guanidine-based QIAzol Lysis Reagent (Qiagen, Valencia, Calif.) using a Tissuelyser II (Qiagen, Valencia, Calif.). The homogenate was extracted with 1-Bromo-3-chloropropane (Sigma-Aldrich, St. Louis, Mo.). RNA was extracted from 0.2 mL of the aqueous phase using the MagMax Technology (ThermoFisher Scientific, Waltham, Mass.) according to the manufacturer's instructions. RNA was quantified using spectrometry at 260 and 280 nm. RT-qPCR assays and reagents from ThermoFisher Scientific (Waltham, Mass.) were used to measure LDHA mRNA level with normalization to Peptidyl-prolyl cis-trans isomerase B (PPIB) mRNA levels. The degree of LDHA mRNA reduction in the LDHA-1-treated groups was calculated as the percent of expression (normalized to PPIB mRNA levels) relative to the average expression level of the control group on the same day, where LDHA mRNA expression in the control group was set at 100%.

LDH Western Blot: Tissue lysates were prepared using TissueLyser II (Qiagen, Valencia, Calif.) with T-PER Tissue Protein Extraction Reagent and protease inhibitor cocktail (ThermoFisher Scientific, Waltham, Mass.). Total protein concentration was measured by BCA Protein Assay (ThermoFisher Scientific, Waltham, Mass.) and equal protein concentrations were resolved by NuPAGE 4-12% Bis-Tris SDS-PAGE (ThermoFisher Scientific, Waltham, Mass.). Electrophoresed proteins were transferred to nitrocellulose membranes using the iBlot Dry Blotting System (ThermoFisher Scientific, Waltham, Mass.) and blocked with Odyssey Blocking Buffer (PBS) (Li-Cor Biosciences, Lincoln, Nebr.). Membranes were then incubated with rabbit anti-LDHA antibody (Cell Signaling Technology, Danvers, Mass.) and with mouse anti-glyceraldehyde 3-phosphate dehydrogenase antibody (Abeam, Cambridge, Mass.). Anti-rabbit IRDye 680 and anti-mouse IRDye 800 secondary antibodies (Li-Cor Biosciences, Lincoln, Nebr.) were used for detection and signal intensity was measured using the Odyssey Infrared Imaging System (Li-Cor Biosciences, Lincoln, Nebr.). The integrated intensity (a measure of the magnitude of the signal and the areas over which it is distributed) was measured for each band. The 'average or median background' methods were used to correct for noise signals. The degree of LDH protein reduction in the LDHA-1-treated groups was calculated as the percent of expression (normalized to GAPDH protein levels) relative to the average expression level of the control group on the same day, where LDH protein expression in the control group was set at 100%.

LDH Activity Assay: Normalized protein concentrations of the tissue extracts prepared for LDH western blot in Section 6.2.2 were evaluated for LDH activity using a Lactate Dehydrogenase Assay Kit (Abeam, Inc., Cambridge, Mass.) according to the manufacturer's instructions. Briefly, tissue extracts were diluted to a concentration of 50 μg/mL in T-PER Tissue Protein Extraction Reagent and then diluted 5-fold into a 96-well plate in duplicate by adding 10 μL of sample into 40 μL of LDH Assay Buffer. A series of standard solutions of Nicotinamide adenine dinucleotide (NADH)

and an LDH positive control were prepared according to the manufacturer's instructions. The plate was mixed, protected from light, and incubated at room temperature for 30 minutes. The absorbance at 450 nanometers was measured 0 and 30 minutes after addition of the Reaction Mix using a SpectraMax MS plate reader (Molecular Devices, Sunnyvale, Calif.). The degree of LDH activity reduction in the LDHA-1-treated groups was calculated as the percent of activity relative to the average activity level of the control group on the same day, where LDH activity in the control group was set at 100%.

Measurement of Ago2-Associated the oligonucleotide using SI-RT-qPCR: Immunoprecipitation of Ago2 protein from snap-frozen monkey liver samples was performed using Dynabeads Protein G. Following isolation of Ago2 protein in the samples, a research-based SL-RT-qPCR method was used to quantify the concentration of LDHA-1 associated with the Ago2 complex. To control for the inter-sample variability in immunoprecipitation, miR-16, an endogenous microRNA that is loaded into the Ago2 complex, was used as a normalizer. Details of the procedure are presented in Appendix 10.2. Only samples from Day 255 were analyzed to obtain information on dose proportionality of RISC-loaded LDHA-1 at high doses where LDHA mRNA reduction is saturated. Determination of LDHA mRNA reduction at Day 309 was deemed sufficient for assessment of pharmacodynamic recovery.

Data Analysis: Graphs were generated in and data were analyzed using GraphPad Prism. One-way ANOVA using Dunnett's multiple comparisons test was performed to compare LDHA mRNA levels (normalized to PPIB mRNA levels), LDH protein levels (normalized to GAPDH protein levels), and LDH activity levels in the LDHA-1-treated groups with that in the control group of the same time point. One-way ANOVA with multiple comparisons was used to compare the concentrations of LDHA-1 incorporated in RISC, with α=0.05. ROUT outlier analysis was performed on individual animal data for miR-16-normalized LDHA- and 1 outlier was identified and excluded from all analyses.

Example 3: Proof of Concept in Study in Humans for RNAi Oligonucleotide Targeting LDHA in the Treatment of Primary Hyperoxaluria The objective of this study was to evaluate safety, tolerability, pharmacokinetics, and pharmacodynamics in humans of single ascending doses of the RNAi oligonucleotide LDHA-1 of Example 1. Secondary endpoints included evaluating the change in 24-hour urinary oxalate excretion from baseline, defined as the mean of two 24-hour collections during screening. The study was divided into two groups:

Group A was designed as a placebo-controlled, single-blind Phase 1 study in 25 normal healthy volunteers (NHVs) enrolled at a single site in the United Kingdom. Group B was designed as an open-label, multi-center study of the LDHA-1 oligonucleotide described in Example 1 in 16 patients with PH, including three cohorts of patients with PH1 dosed at 1.5, 3, and 6 mg/kg, and a fourth PH2-only cohort with flexible dosing. Group B patients were being enrolled at five sites in the European Union (EU) and one site in the U.S.

Figure 8A:
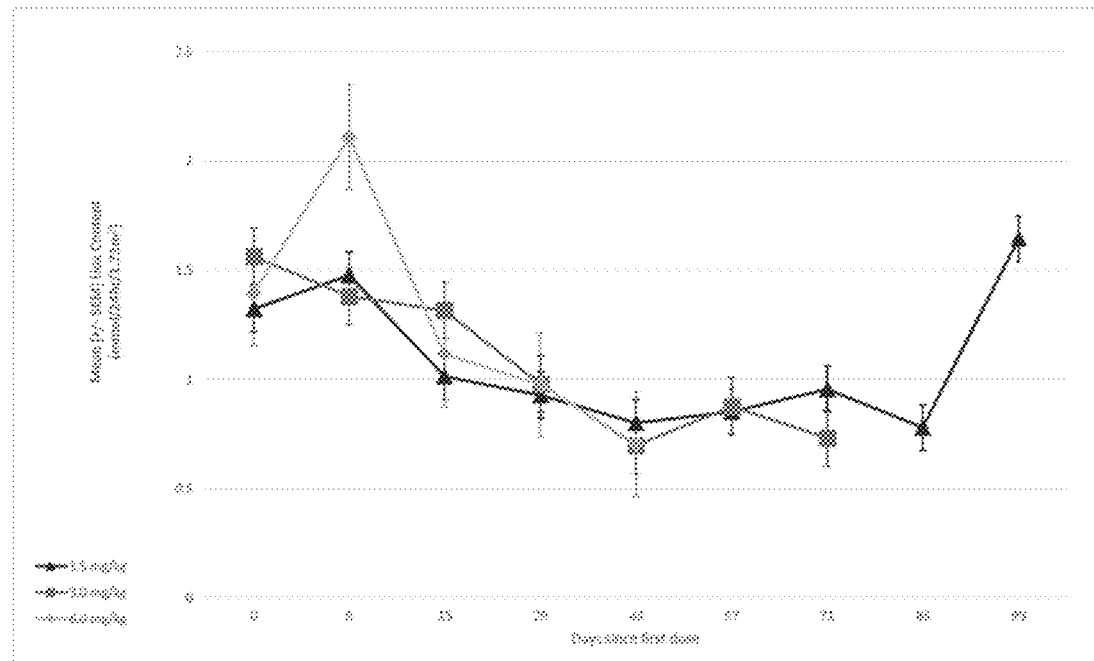
FIGS. 8A-8B are graphs showing the effect of the oligonucleotide as shown in FIG. 3 at different doses (1.5 mg/kg, 3 mg/kg, or 6 mg/kg) in PH patients in an open-label, multi-center study.
Figure 8B:
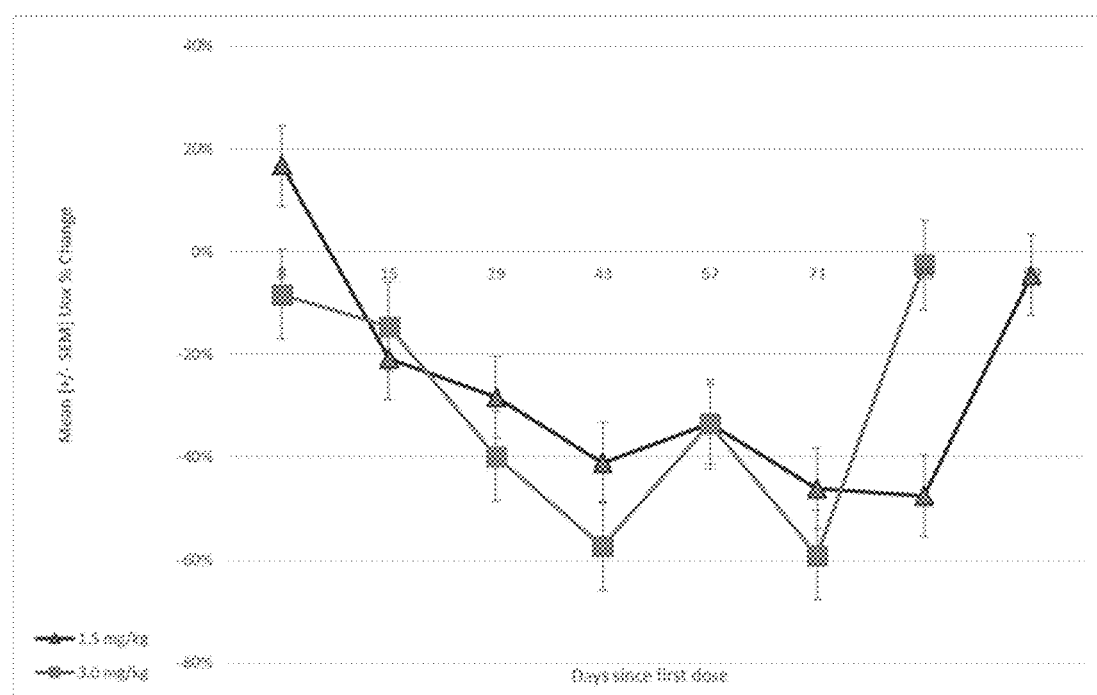

In the first Group B cohort (1.5 mg/kg), initial results following a single administration of the RNAi oligonucleotide showed that three of four adult patients to date reached near-normal concentrations (≤60 mmol/24 hr) of urinary oxalate between Days 43 and 57. The fourth adult, whose baseline urinary oxalate level was 2.28 mmol/24 hr, exhibited substantial reductions, with an observation beyond day 71 showing significant reduction for that patient (urinary oxalate (UOX)<1.0 mmol/24 hr). The results are summarized in FIGS. 8A and 8B.

In the second Group B cohort (3 mg/kg), two of four adult patients to date reached normal urinary oxalate concentrations (≤0.46 mmol/24 hr) between Days 29 and 43. Both of the other patients also had substantial oxalate reductions. One patient in this group had elevated plasma oxalate levels. Nevertheless, during treatment with LDHA-1, plasma oxalate was reduced to normal levels. The results are summarized in FIGS. 8A and 8B.

The one adult patient with PH2 in the fourth Group B cohort also experienced a substantial reduction in 24-hour urinary oxalate excretion (more than 35%) on at least one of the sampling days (day 57).

Further, only three mild-to-moderate injection site reactions were observed. All were transient (<72 hours) and resolved without intervention.

In summary, administration of LDHA-1 brought urinary oxalate levels into the normal range (defined as 24-hour excretion≤0.46 mmol) or near-normal range (defined as 24-hour excretion≤0.6 mmol) in a majority of the 8 assessed primary hyperoxaluria type 1 and type 2 (PH1 and PH2) patients. All of the assessed patients experienced substantial and clinically significant reductions in urinary oxalate (defined as >30% reduction compared to baseline). Assessed patients are those patients for which data is available through Week 6, or Day 43. All assessed patients are adults and include seven patients with PH1 and one patient with PH2.

These data above constitute clinical proof of concept for the RNAi oligonucleotide LDHA-1 of Example 1 in humans and also show that LDHA-1 was safe and well-tolerated. The results demonstrate potency and duration of action following administration of a single dose, and are consistent with and supportive of quarterly administration to subjects.

The magnitude of urinary oxalate reduction, coupled with the duration of action validate therapeutic targeting of lactase dehydrogenase, which is involved in the ultimate step of hepatic oxalate production. Based on this mechanism of action, LDHA-1 can be used in the treatment of all types of primary hyperoxaluria. The substantial reductions in urinary oxalate confirm that the platform can effectively reduce target gene expression in humans and the use of such RNAi therapeutics to treat multiple forms of primary hyperoxaluria.

Materials and Methods for Example 3

LDHA-1 Molecular Structure (See Also Example 1, FIG. JA and FIG. 3)

Sense Strand: SEQ ID NO. 2

5' mA-S-mU-fG-mU-fU-mG-mU-fC-fC-fU-fU-mU-fU-mUfA-mU-fC-mU-mG-mA-mG-mC-mA-mG-mC-mC-

[ademG-GalNAc]-[ademA-GalNAc]-[ademA-GalNAc]-

[ademA-GalNAc]-mG-mG-mC-mU-mG-mC 3'

Hybridized to:
Antisense Strand: SEQ ID NO. 1

5' [MePhosphonate-4O-mU]-S-fC-S-fA-S-fG-fA-mUfA-mA-fA-fA-mA-mG-mG-fA-mC-fA-mA-fC-mA-mU-S-mG- S-mG 3'

Legend:

| | |
|---|---|
| mX: | 2'-O-methyl ribonucleoside |
| fX | 2'-fluoro-deoxyribonucleoside |
| [ademA-GalNAc]: | 2'-O-GalNAc-modified adenosine |
| [ademG-GalNAc]: | 2'-O-GalNAc-modified guanosine |
| [MePhosphonate-4O-mU]: | 4'-O-monomethylphosphonate-2'-O-methyl uridine |
| Linkages: | "-" denotes phosphodiester |
| | "-S-" denotes phosphorothioate |

Pharmaceutical Development

The drug product was a sterile liquid drug product consisting of LDHA-1 as a solution in WFI (Water for Injection) for SC administration. The formulation used (170 mg/ml concentration of LDHA-1 in WFI at pH 6.2-8.2) was selected based on pH, osmolality (200-300 mOsm/kg), viscosity, and compatibility with the route of administration.

Diagnosis and Criteria for Inclusion/Exclusion

Group A Criteria for Inclusion:

1. Subject must have understood the full nature and purpose of the study, including possible risks and side effects, and is willing and able to comply with all study procedures and restrictions.

2. Male or female subjects between 18 and 55 years of age, inclusive.

3. Subject must have had a body mass index (BMI) 19.0 to 32 Kg/m2, inclusive.

4. Non-smokers, at least 1-month tobacco free, and willing to remain tobacco free through EOS. Subjects must also have been free from nicotine-containing products (e.g., nicotine patch.)

5. Subjects must have been otherwise healthy. Healthy status was defined based on the opinion of the PI by the absence of evidence of any clinically significant, active, or chronic disease following a detailed medical and surgical history, a complete physical examination including vital signs, 12-lead ECG, hematology, blood chemistry, serology, and urinalysis.

6. Subjects must had hematology and clinical chemistry tests and urine analyses within the normal range, unless abnormalities had been classified as Not Clinically Significant (NCS) by the Investigator or qualified designee. Liver panel tests (ALT and AST) must have been normal. Retests could have been conducted one time for liver panel results.

7. Females and males as well as female partner(s) of male subjects who are of childbearing potential must have been willing to use a highly effective and approved contraceptive method (s) from the date of informed consent until 12 weeks after the last dose of IMP. A highly effective method of contraception was defined as fulfilling at least one of the following:

a. Strict abstinence: When this was in line with the preferred and usual lifestyle of the patient. [Periodic abstinence (e.g., calendar, ovulation, symptom-thermal, post-ovulation methods) and withdrawal were not acceptable methods of contraception.]

b. Surgically sterile (having undergone one of the following surgical procedures: hysterectomy, bilateral tubal ligation, bilateral oophorectomy, or bilateral salpingectomy) and at least 6 weeks post-sterilization.

c. Combined hormonal oral contraceptive (estrogen and progesterone), implanted, or injectable contraceptive on a stable dose for at least 1 month prior to the screening visit plus a barrier method. Combined hormonal contraception was considered a highly effective method of contraception only if it was associated with inhibition of ovulation. If associated with inhibition of ovulation, progesterone-only hormonal contraception is also considered a highly effective method of contraception.

d. Intrauterine devices plus condoms. Hormonal intrauterine device (IUD) inserted at least 1 month prior to the screening visit.

e. Double-barrier methods [e.g., Condom and Occlusive cap (diaphragm or cervical/vault caps) with spermicidal foam/gel/film/cream/suppository]. Of note, a female condom and a male condom, or two male condoms, should not have been used together as friction between the two can result in either product failing.

f. Vasectomized partner (at least 6 months post-procedure) prior to the screening visit.

8. Postmenopausal females: defined as 12 months with no menses prior to screening and a serum FSH>26 IU/L at screening visit.

9. For females: a negative pregnancy test at screening and Day 0 visit.

Group B—PH Patient Inclusion Criteria

PH patients must have met all of the following criteria to be eligible for participation in this study.

1. Patient and/or patient's parent or guardian if the patient was a minor (defined as patient<18 years of age, or younger than the age of majority, according to local regulations), a. Must have understood the full nature and purpose of the study, including possible risks and side effects.

b. Must have been willing and able to comply with all study procedures including collection of 24-hr urine samples.

c. Must have provided informed consent. Adolescents (12 to <18 years of age, or older than 12 years but younger than the age of majority, according to local regulations) must have been able to provide written assent for participation. For children younger than 12 years of age, assent would have been based on local regulations.

2. Male or female, at least 6 years of age at the time of obtaining informed consent.

3. Patient must have had a minimum body weight of 25 Kg.

4. Documented diagnosis of PH1 or PH2, confirmed by genotyping (historically available genotype information is acceptable for study eligibility).

5. 24-hr urine oxalate excretion≥0.7 mmol for patients 18 years and older, or ≥0.7 mmol per 1.73 m2 body surface area (BSA) for patients less than 18 years of age, on at least one of the two assessments conducted in the screening period, with less than 30% variation between both oxalate measurements.

6. eGFR≥30 mL/min normalized to 1.73 m2 BSA calculated using the Modification of Diet in Renal Disease (MDRD) formula in adults (age≥18 years), or the formula by Schwartz in patients 6 to <18 years old 7. Males, female patients of childbearing potential and female partners of male patients of childbearing potential must have been willing to use a highly effective and approved contraceptive method(s) from the date of informed consent until 12 weeks after the last dose of IMP. A highly effective method of contraception would have been defined as fulfilling at least one of the following:

a. Strict abstinence: When this was in line with the preferred and usual lifestyle of the patient. [Periodic abstinence (e.g., calendar, ovulation, symptom-thermal, post-ovulation methods) and withdrawal would not have been acceptable methods of contraception.]

b. Surgically sterile (having undergone one of the following surgical procedures: hysterectomy, bilateral tubal ligation, bilateral oophorectomy, or bilateral salpingectomy) and at least 6 weeks post-sterilization.

c. Combined hormonal oral contraceptive (estrogen and progesterone), implanted, or injectable contraceptive on a stable dose for at least 1 month prior to the screening visit plus a barrier method. Combined hormonal contraception would have been considered a highly effective method of contraception only if it was associated with inhibition of ovulation. If associated with inhibition of ovulation, progesterone-only hormonal contraception would have also been considered a highly effective method of contraception.

d. Intrauterine devices plus condoms. Hormonal IUD inserted at least 1 month prior to the screening visit.

e. Double-barrier methods [e.g., Condom and Occlusive cap (diaphragm or cervical/vault caps) with spermicidal foam/gel/film/cream/suppository]. Of note, a female condom and a male condom, or two male condoms, should not have been used together as friction between the two can result in either product failing.

f. Vasectomized partner (at least 6 months post-procedure) prior to the screening visit.

8. Postmenopausal females: defined as 12 months with no menses prior to screening and a serum FSH>26 IU/L at screening.

9. For WOCP: a negative pregnancy test at screening and Day 0

10. Patients with PH1 receiving pyridoxine at stable doses at least 4 weeks prior to study entry must have been willing to remain on the same stable dose during the study. In the unlikely event that a patient with PH2 was receiving pyridoxine, this should have been discontinued at least 4 weeks prior to study entry Group A—NHV Exclusion Criteria Normal Health Volunteers meeting any of the following criteria would have been excluded from this study:

1. Presence of any medical condition or co-morbidities that would interfere with study compliance or data interpretation or potentially impact subject safety including, but not restricted to:

a. severe intercurrent illness b. routine vaccination within 30 days prior to dosing and through EOS visit c. known causes of active liver disease/injury or transaminase elevation (e.g., alcoholic liver disease, Nonalcoholic fatty liver disease/steatohepatitis (NAFLD/NASH))

d. physician concerns about excess alcohol consumption e. routine or chronic use of more than 3 grams of paracetamol daily.

2. History of kidney stones.

3. Women who were pregnant, lactating, or planning to attempt to become pregnant during this study or within 90 days after last dosing of IMP.

4. Males with female partners who were planning to attempt to become pregnant during this study or within 90 days after last dosing of IMP.

5. Use of any investigational agent within 90 days before the first dose of study medication. If a subject has participated in prior siRNA or antibody studies, a washout period of at least 6 months before the first administered dose in this study would have been required.

6. Strenuous activity, sunbathing, and contact sports within 48 hrs (2 days) prior to dose administration and through to the EOS visit or Day 29.

7. History of donation of more than 450 mL of blood within 90 days prior to dosing in the clinical research center or planned donation less than 30 days after receiving IMP.

8. Plasma or platelet donation within 7 days of dosing and throughout the entire study.

9. History of alcohol consumption exceeding more than 21 units in males, 14 units in females, per week as determined by the Investigator. Alcohol consumption would have been prohibited 48 hrs prior to admission to the clinical facility and until the end of study.

10. Positive screening test for hepatitis B surface antigen (HBsAg), anti-hepatitis C virus (HCV) antibodies, or anti-human immunodeficiency virus (HIV) 1 and 2 antibodies. If subject had been tested in the past 3 months, historical data may have been used.

11. History of one or more of the following reactions to an oligonucleotide-based therapy a. Severe thrombocytopenia b. Hepatotoxicity c. Severe flu-like symptoms leading to discontinuation of therapy d. Localized skin reaction from the injection (Grade 3 or higher) leading to discontinuation of therapy.

e. Coagulopathy/clinically important prolongation of clotting time

Other Restrictions:

All regular non-topical medication and non-regular medication (including over-the-counter medication, health supplements, and chronic dosing of herbal remedies such as St. John's Wort extract) must have been stopped at least 14 days prior to admission to the clinical research center through and including EOS visit. An exception would have been made for paracetamol (acetaminophen), which would have been allowed up to admission to the clinical research center. However, NSAIDs such as ibuprofen, aspirin, naproxen, etc. must have been stopped at least 14 days prior to admission to the clinical research center. Subjects should not have engaged in vigorous exercise during study participation (i.e., between screening and EOS visits). Throughout the study, subjects would have been required to avoid oxalate-rich foods and to eat moderate amounts of protein and calcium, not to exceed national dietary guidelines. Protein shakes must have been avoided.

Group B—PH Patient Exclusion Criteria

PH patients meeting any of the following criteria would have been excluded from this study:

1. Prior renal and/or hepatic transplantation.

2. Currently receiving dialysis.

3. Documented evidence of clinical manifestations of systemic oxalosis.

4. Participation in any clinical study where they received an investigational medical product within 4 months before enrollment. For IMPs with the potential to reduce Uox and/or plasma oxalate, these concentrations must have returned to historical baseline levels.

a. If patient participated in an earlier cohort in this study, a minimum of 8 weeks must have elapsed prior to re-enrollment and urinary oxalate excretion must have returned to ≥80% of baseline.

5. Presence of any medical condition or co-morbidities that would interfere with study compliance or data interpretation or potentially impact patient safety including, but not restricted to:

a. severe intercurrent illness b. routine vaccination within 30 days prior to dosing and through EOS visit c. known causes of active liver disease/injury or transaminase elevation (e.g., alcoholic liver disease, Nonalcoholic fatty liver disease/steatohepatitis (NAFLD/NASH)

d. physician concerns about excess alcohol consumption e. routine or chronic use of more than 3 grams of acetaminophen daily.

6. History of alcohol consumption exceeding more than 21 units in males, 14 units in females, per week as determined by the Investigator.

7. Women who are pregnant, lactating, or planning to attempt to become pregnant during this study or within 90 days after last dosing of IMP.

8. Liver function test (LFT) abnormalities: ALT and/or AST>1.5 times ULN for age and gender.

9. History of one or more of the following reactions to an oligonucleotide-based therapy a. Severe thrombocytopenia b. Hepatotoxicity c. Severe flu-like symptoms leading to discontinuation of therapy d. Localized skin reaction from the injection (Grade 3 or higher) leading to discontinuation of therapy.

e. Coagulopathy/clinically important prolongation of clotting time

Other Restrictions:

Patients should also have avoided taking Vitamin C supplements for 24 hrs before and during the 24-hr urine specimen collections, and for 24 hrs before the PD blood collections. Patients should not have engaged in vigorous exercise during study participation (i.e., between screening and EOS visits). Throughout the study patients should have been required to avoid oxalate-rich foods and to eat moderate amounts of protein and calcium, not to exceed national dietary guidelines. Protein shakes must have been avoided.

Measurement of Urinary Oxalate (UOX) Levels

A 24-hour urine sample was obtained from the patient and an aliquot was acidified to improve the solubility of the oxalate. Generally, oxalate is insoluble, and forms crystals that can be solubilized in acidic conditions. The solubilized UOX was then subject to HPLC analysis to determine its level.

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

What is claimed is:

1. An oligonucleotide for reducing expression of Lactate dehydrogenase A (LDHA), the oligonucleotide comprising an antisense strand having a sequence set forth as UCAGAUAAAAAGGACAACAUGG (SEQ ID NO: 1) and a sense strand having a sequence set forth as AUGUUGU-CCUUUUUAUCUGAGCAGCCGAAAGGCUGC (SEQ ID NO: 2), wherein one or more of the nucleotides of the -GAAA- sequence on the sense strand is conjugated to a monovalent GalNac moiety through an acetal linker, and wherein the nucleotides of the oligonucleotide are modified, wherein all of positions 1, 2, 4, 6, 7, 12, 14, 16, 18-26, and 31-36 of the sense strand and positions 1, 6, 8, 11-13, 15, 17, and 19-22 of the antisense strand are modified with a 2'-O-methyl, and wherein all of positions 3, 5, 8-11, 13, 15, or 17 of the sense strand and positions 2-5, 7, 9, 10, 14, 16, and 18 of the antisense strand are modified with a 2'-fluoro.

2. The oligonucleotide of claim 1, wherein each of the nucleotides of the -GAAA- sequence on the sense strand is conjugated to a monovalent GalNac moiety.

3. The oligonucleotide of claim 1, wherein the oligonucleotide has a phosphorothioate linkage between each of: positions 1 and 2 of the sense strand, positions 1 and 2 of the antisense strand, positions 2 and 3 of the antisense strand, positions 3 and 4 of the antisense strand, positions 20 and 21 of the antisense strand, and positions 21 and 22 of the antisense strand.

4. The oligonucleotide of claim 1, wherein the antisense strand comprises a 4'-oxymethylphosphonate at a 5'-terminal nucleotide.

5. An oligonucleotide for reducing expression of Lactate dehydrogenase A (LDHA), the oligonucleotide comprising an antisense strand having a sequence set forth as UCAGAUAAAAAGGACAACAUGG (SEQ ID NO: 1) and a sense strand having a sequence set forth as AUGUUGU-CCUUUUUAUCUGAGCAGCCGAAAGGCUGC (SEQ ID NO: 2), wherein one or more of the nucleotides of the -GAAA- sequence on the sense strand is conjugated to a monovalent GalNac moiety through an acetal linker, wherein the nucleotides of the oligonucleotide are modified with a 2'-O-methyl or a 2'-fluoro, wherein at least one internucleotide linkage is modified as a phosphorothioate linkage, and wherein the antisense strand comprises a 4'-phosphate analog at a 5'-terminal nucleotide, and wherein all of positions 1, 2, 4, 6, 7, 12, 14, 16, 18-26, and 31-36 of the sense strand and positions 1, 6, 8, 11-13, 15, 17, and 19-22 of the antisense strand are modified with a 2'-O-methyl, and wherein all of positions 3, 5, 8-11, 13, 15, or 17 of the sense strand and positions 2-5, 7, 9, 10, 14, 16, and 18 of the antisense strand are modified with a 2'-fluoro.

6. The oligonucleotide of claim 5, wherein each of the nucleotides of the -GAAA- sequence on the sense strand is conjugated to a monovalent GalNac moiety.

7. The oligonucleotide of claim 5, wherein the antisense strand comprises a 4'-oxymethylphosphonate at a 5'-terminal nucleotide.

8. The oligonucleotide of claim 5, wherein the oligonucleotide has a phosphorothioate linkage between each of: positions 1 and 2 of the sense strand, positions 1 and 2 of the antisense strand, positions 2 and 3 of the antisense strand, positions 3 and 4 of the antisense strand, positions 20 and 21 of the antisense strand, and positions 21 and 22 of the antisense strand.

9. An oligonucleotide for reducing expression of Lactate dehydrogenase A (LDHA) having the structure as shown in FIG. 1A, wherein the -GAAA- sequence at positions 27-30 of the sense strand has the structure:

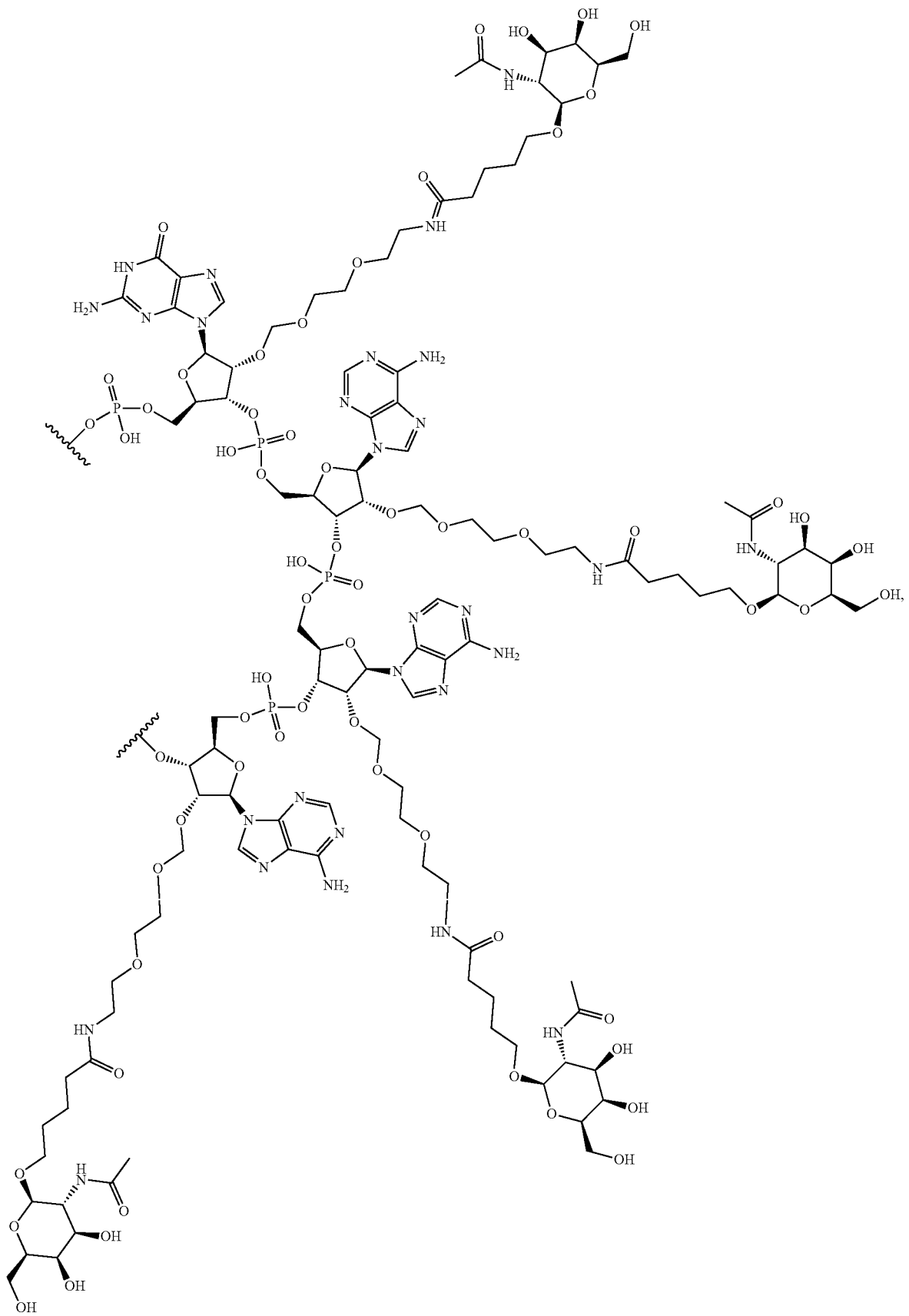 [SMILES: *O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@H]1[C@@H](OCOCCOCCNC(=O)CCCCO[C@@H]2O[C@H](CO)[C@H](O)[C@H](O)[C@H]2NC(C)=O)[C@H](n2cnc3c(=O)[nH]c(N)nc32)O[C@@H]1COP(=O)(O)O*]

and
the nucleotide at position 1 of the antisense strand has the structure:
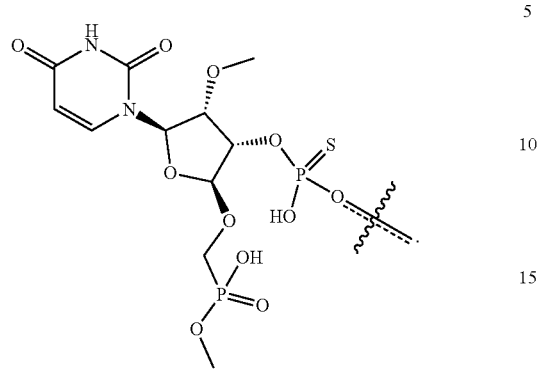
10. The oligonucleotide of claim 9, wherein the oligonucleotide has the structure:

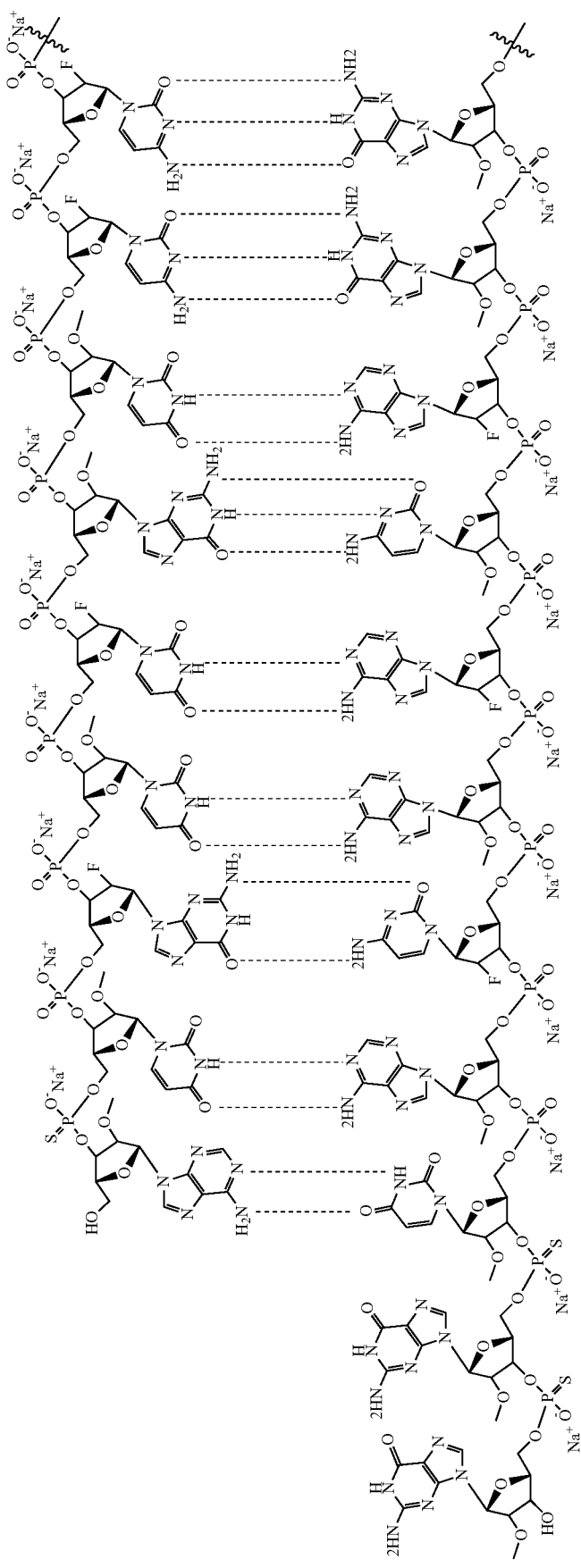

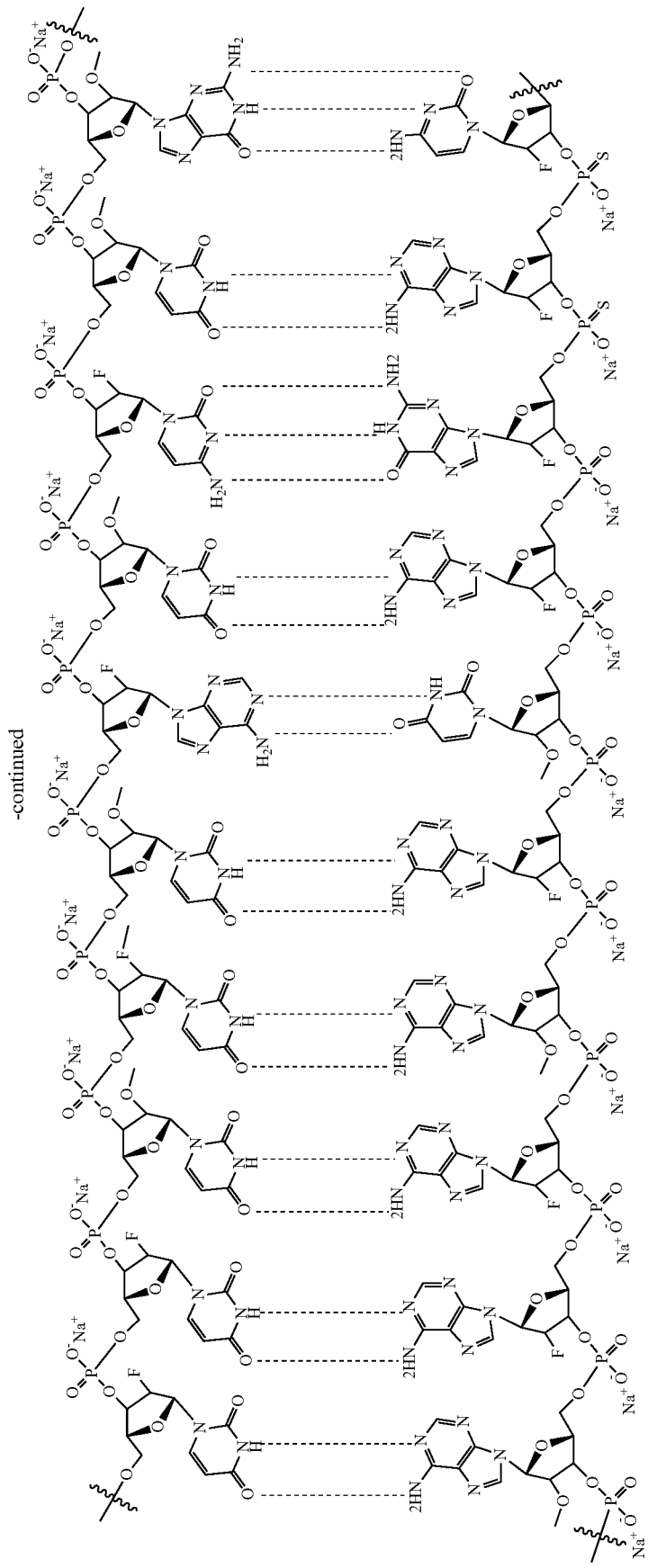

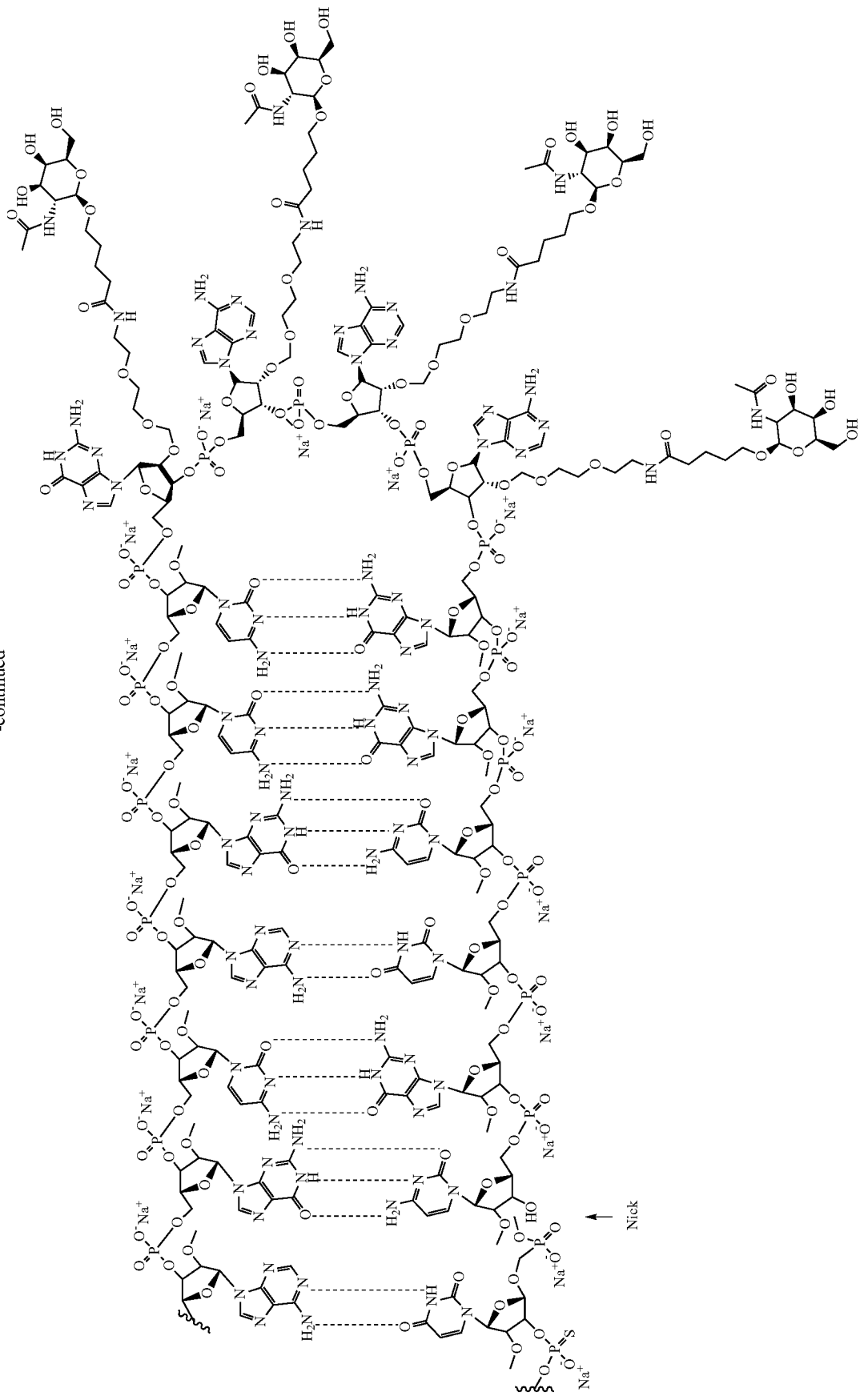

11. A composition comprising the oligonucleotide of claim 1 and Na$^+$ counterions.

12. A method of reducing expression of Lactate dehydrogenase A (LDHA) in a subject, the method comprising administering the composition of claim 11 to the subject.

13. The method of claim 12, wherein the subject has or is at risk of having PH1, PH2, PH3, and/or idiopathic hyperoxaluria.

14. The method of claim 13, wherein the composition is administered to the subject intravenously or subcutaneously.

15. A composition comprising the oligonucleotide of claim 9 and Na$^+$ counterions.

16. A method of reducing expression of Lactate dehydrogenase A (LDHA) in a subject, the method comprising administering the composition of claim 15 to the subject.

17. The method of claim 16, wherein the subject has or is at risk of having PH1, PH2, PH3, and/or idiopathic hyperoxaluria.

18. A composition comprising the oligonucleotide of claim 5 and Na$^+$ counterions.

19. A method of reducing expression of Lactate dehydrogenase A (LDHA) in a subject, the method comprising administering the composition of claim 18 to the subject.

20. The method of claim 19, wherein the subject has or is at risk of having PH1, PH2, PH3, and/or idiopathic hyperoxaluria.

* * * * *

UNITED STATES PATENT AND TRADEMARK OFFICE
CERTIFICATE OF CORRECTION

PATENT NO. : 11,661,604 B2
APPLICATION NO. : 17/022696
DATED : May 30, 2023
INVENTOR(S) : Bob D. Brown et al.

It is certified that error appears in the above-identified patent and that said Letters Patent is hereby corrected as shown below:

In the Claims

At Column 34, Claim number 9, Lines 64-65 please replacing: "having the structure as shown in FIG. 1A," with the following:

"comprising an antisense strand having a sequence set forth as UCAGAUAAAAAGGACAACAUGG (SEQ ID NO: 1) and a sense strand having a sequence set forth as AUGUUGUCCUUUUUAUCUGAGCAGCCGAAAGGCUGC (SEQ ID NO: 2), wherein one or more of the nucleotides of the GAAA sequence on the sense strand is conjugated to a monovalent GalNac moiety through an acetal linker, and
wherein the nucleotides of the oligonucleotide are modified, wherein all of positions 1, 2, 4, 6, 7, 12, 14, 16, 18-26, and 31-36 of the sense strand and positions 1, 6, 8, 11-13, 15, 17, and 19-22 of the antisense strand are modified with a 2′-O-methyl, and wherein all of positions 3, 5, 8-11, 13, 15, or 17 of the sense strand and positions 2-5, 7, 9, 10, 14, 16, and 18 of the antisense strand are modified with a 2′-fluoro,"

Signed and Sealed this
Twenty-first Day of November, 2023

*Katherine Kelly Vidal*

Katherine Kelly Vidal
*Director of the United States Patent and Trademark Office*